(12) United States Patent
Shi et al.

(10) Patent No.: US 8,273,777 B2
(45) Date of Patent: Sep. 25, 2012

(54) GLUCOKINASE ACTIVATORS AND METHODS OF USING SAME

(75) Inventors: Yan Shi, Flourtown, PA (US); Peter T. W. Cheng, Princeton, NJ (US); Ying Wang, Princeton, NJ (US); Denis E. Ryono, Minneapolis, MN (US)

(73) Assignee: Bristol-Meyer Squibb Company, Princeton, NJ (US)

( * ) Notice: Subject to any disclaimer, the term of this patent is extended or adjusted under 35 U.S.C. 154(b) by 51 days.

(21) Appl. No.: 12/871,226

(22) Filed: Aug. 30, 2010

(65) Prior Publication Data
US 2010/0324071 A1    Dec. 23, 2010

Related U.S. Application Data

(62) Division of application No. 12/179,648, filed on Jul. 25, 2008, now Pat. No. 7,812,048.

(60) Provisional application No. 60/952,273, filed on Jul. 27, 2007.

(51) Int. Cl.
*A61K 31/4439* (2006.01)
*A61K 31/426* (2006.01)
*C07D 419/12* (2006.01)
*C07D 277/56* (2006.01)

(52) U.S. Cl. ............... 514/365; 514/342; 546/269.7; 548/200

(58) Field of Classification Search .......... 548/200; 514/365
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,261,730 A | 4/1981 | Bollinger et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau et al. |
| 5,612,359 A | 3/1997 | Murugesan |
| 5,686,104 A | 11/1997 | Mills et al. |
| 5,691,322 A | 11/1997 | Robl |
| 5,712,279 A | 1/1998 | Biller et al. |
| 5,712,396 A | 1/1998 | Magnin et al. |
| 5,739,135 A | 4/1998 | Biller et al. |
| 5,753,675 A | 5/1998 | Wattanasin |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson et al. |
| 5,885,983 A | 3/1999 | Biller et al. |
| 5,962,440 A | 10/1999 | Sulsky |
| 6,043,265 A | 3/2000 | Murugesan et al. |
| 6,414,002 B1 | 7/2002 | Cheng et al. |
| 6,414,126 B1 | 7/2002 | Ellsworth et al. |
| 6,548,481 B1 | 4/2003 | Demuth et al. |
| 6,548,529 B1 | 4/2003 | Robl et al. |

(Continued)

FOREIGN PATENT DOCUMENTS

DE    3214227 A    10/1983

(Continued)

OTHER PUBLICATIONS

McKerrecher et al. Bioorganic & Medicinal Chemistry Letters 2005, 15, 2103-2106.*

(Continued)

*Primary Examiner* — Joseph Kosack
*Assistant Examiner* — Matthew Coughlin
(74) *Attorney, Agent, or Firm* — Burton Rodney

(57) ABSTRACT

Compounds are provided which are activators of the enzyme glucokinase and thus are useful in treating diabetes and related diseases, which compounds have the structure

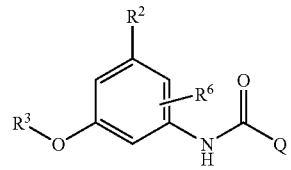

where Q is

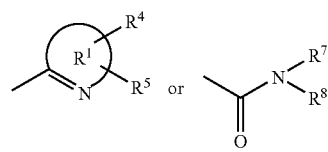

and $R^1$, $R^2$, $R^3$, $R^4$, $R^5$, $R^6$, $R^7$ and $R^8$ are as defined herein or a pharmaceutically acceptable salt thereof.
A method for treating diabetes and related diseases employing the above compounds is also provided.

11 Claims, No Drawings

U.S. PATENT DOCUMENTS 6,653,314 B2 11/2003 Cheng et al.

FOREIGN PATENT DOCUMENTS

| | | |
|---|---|---|
| EP | 0 221 025 | 5/1987 |
| EP | 0 142 146 | 8/1988 |
| EP | 1 177 791 | 2/2002 |
| EP | 1 690 863 | 8/2006 |
| FR | 2 596 393 | 4/1986 |
| GB | 2 205 837 | 12/1988 |
| JP | 2003 300875 | 10/2003 |
| WO | WO 86/03488 | 6/1986 |
| WO | WO 86/07054 | 12/1986 |
| WO | WO 96/38144 | 12/1996 |
| WO | WO 97/12613 | 4/1997 |
| WO | WO 97/12615 | 4/1997 |
| WO | WO 97/21993 | 6/1997 |
| WO | WO 99/00353 | 1/1999 |
| WO | WO 99/38501 | 8/1999 |
| WO | WO 99/43663 | 9/1999 |
| WO | WO 99/46272 | 9/1999 |
| WO | WO 99/67278 | 12/1999 |
| WO | WO 99/67279 | 12/1999 |
| WO | WO 00/01389 | 1/2000 |
| WO | WO 00/39077 | 7/2000 |
| WO | WO 00/69849 | 11/2000 |
| WO | WO01/05769 | 1/2001 |
| WO | WO03/035621 | 5/2003 |
| WO | WO03/037332 | 5/2003 |
| WO | WO 03/106427 | 12/2003 |
| WO | WO 2004076420 A1 | 9/2004 |
| WO | WO 2004/099155 | 11/2004 |
| WO | WO2005/032493 | 4/2005 |
| WO | WO 2005/080359 | 9/2005 |
| WO | WO 2005/121110 | 12/2005 |
| WO | WO2006/112549 | 10/2006 |
| WO | WO 2006122011 A2 * | 11/2006 |
| WO | WO2007/061923 | 5/2007 |

OTHER PUBLICATIONS

CAS Registry No. 926883-30-9, which entered STN on Mar. 18, 2007.*

CAS Registry No. 313643-94-6, which entered STN on Jan. 12, 2001.*

Hadden, M.K. et al., "Cytotoxic small molecule dimmers and their inhibitory activity against human breast cancer cells", Bioorganic & Medicinal Chemistry Letters, vol. 17, No. 18, 2007, pp. 5063-5067.

McKerrecher, D. et al., "Discovery synthesis and biological evaluation of novel glucokinase activators", Bioorganic & Medicinal Chemistry Letters, vol. 15, No. 8, 2005, pp. 2103-2106.

Patani, et al., Chem. Rev., vol. 96, pp. 3147-3176 (1996).

Rautio, et al., Nature Reviews Drug Discovery, vol. 7, pp. 255-270 (2008).

Testa, B., Current Opinion in Chemical Biology, vol. 13, pp. 338-344 (2009).

Smith, D.A., Current Opinion in Drug Discovery & Development, vol. 10, pp. 550-559 (2007).

Sheridan, R.P., J. Chem. Inf. Comput. Sci., vol. 42, pp. 103-108 (2002).

Wermuth, C.G., Molecular variations based on Isosteric replacements. In the Practice of Medicinal Chem., Wermuth, D.G. Eds.; pp. 202-237 (1996).

Wang, et al., Drug Delivery: Principles and Applications, 2005 John Wiley & Sons, Inc. Publication, Section 8.3, pp. 136-137.

Arbeeny, C. et al. "The Metabolic Syndrome: From Pathophysiology to Novel Treatment Strategies", Curr. Med. Chem.— Imm. Endoc. & Metab. Agents, 1:1-24 (2001).

Ashworth et al., "2-Cyanopyrrolidides as Potent, Stable Inhibitros of Deipeptidyl Peptidase IV", Biog. & Med. Chem. Lett., vol. 6, No. 10, pp. 1163-1166, (1996).

Ashworth et al., "4-Cyanothiazolidides as Very Potent, Stable Inhibitors of Dipeptidyl Peptidase IV", Biorg. & Med. Chem. Lett., vol. 6, No. 22, pp. 2745-2748, (1996).

Biller et al., "Isoprenoid (Phosphinylmethyl)phosphonates as Inhibitor of Squalene Synthetase", Amer. Chem. Soc., vol. 31, No. 10, pp. 1869-1871 (1988).

Biller et al., "Squalene Synthetase Inhibitors", Curr. Pharm. Des, 2, pp. 1-40 (1996).

Bundgaard, H., Design of Prodrugs, Elsevier, 1985.

Bundgaard, H. et al., A Textbook of Drug Design and Development, Chapter 5, pp. 113-191 (Harwood Academic Publishers, 1991).

Capson, T.L., "Synthesis and Evaluation of Ammonium Analogs of Carbocationic Intermediates in Squalene Biosynthesis", Dept. Med. Chem. U of Utah, Table of Contents pp. 16, 17, 40-43, 48-51, Summary, (1987).

Corey, E. J. et al, "Application of Unreactive Analogs of Terpenoid Pyrophosphates of Studies of Multistep Biosynthesis. Demonstration That 'Presqualene Pyrophosphate' is Essential Intermediate on the Path to Squalene", J. Amer. Chem. Soc. 98, pp. 1291-1293 (1976).

Cornicelli, J.A. et al., "15-Lipoxygenase and Its Inhibition: A Novel Therapeutic Target for Vascular Disease", Current Pharmaceutical Design, vol. 5, No. 1, pp. 11-20 (1999).

Ford, E.S. et al., "Prevalence of the Metabolic Syndrome Among US Adults", J. Am. Med. Assoc., 287:356-359 (2002).

Fyfe, M.C. et al., "Glucokinase Activator PSN-GK1 Displays Enhanced Antihyperglycaemic and Insulinotropic Actions", Diabetologia, 50:1277 (2007).

Ghiselli, G., "The pharmacological profile of FCE 27677: a novel ACAT inhibitor with potent hypolipdemic activity mediated by selective suppression of the hepatic secretion of ApoB100-containing lipoprotein", Cardiovasc. Drug Rev. 16(1):16-30(1998).

Green, T.W. et al., Protecting Groups in Organic Synthesis, 1999.

Hera, S., "Ileal Na+/bile acid Contransporter Inhibitors", Drugs of the Future, 24(4), pp. 425-430 (1999).

Hertzog, D.L., "Recent advances in the cannabinoids", Expert. Opin. Ther. Patents, 14:1435-1452 (2004).

Hughes, T.E. et al., "(1-[[[2-[(5-Cyanopyridin-2-yl)amino]ethyl]amino]acetyl]-2- cyano-(S)-pyrrolidine), a Slow-Binding Inhibitor of Dipeptidyl Peptidase IV", Biochem. 38, pp. 11597-11603 (1999).

Krause, B.R. et al. "ACAT Inhibitors: Physiologic Mechanisms for Hypolipidemic and Anti-Atherosclerotic Activities in Experimental Animals", Inflammation: Mediators and Pathways, CRC Press Inc, publ., Ruffolo, Jr., R.R. et al., eds., pp. 173-198 (1995).

Lange, A.J. et al., "Expression and site-directed mutagenesis of hepatic glucokinase", Biochem., J., 277:159-163 (1991).

Li, H. et al., "3-(Diethoxyphosphoryloxy)-1,2,3-benzotriazin-4(3H)-one (DEPBT): A new coupling reagent with remarkable resistance to racemization", Org. Lett., 1:91 (1991).

Liag, Y. et al., "Variable effects of maturity-onset-diabetes-of-youth-MODY-associated glucokinase mutations on substrate interactions and stability of the enzyme", Biochem. J., 309:167-173 (1995).

Matschinsky, F.M. et al., "The Network of Glucokinase-Expressing Cells in Glucose Homeostasis and the Potential of Glucokinase Activators for Diabetes Therapy", Diabetes, 55:1 (2006).

Matschinsky, F.M. et al., Glucokinase and Glycemic Disease from Basics to Novel Therapeutics, Karger, publ., Chapter 6, pp. 360-378 (2004).

McClard, R.W. et al., "Novel Phosphonylphosphinyl (P-C-P-C) Analogues of Biochemically Interesting Diphosphates. Syntheses and Properties of P-C-P-C Analogues of Isopentenyl Diphosphate and Dimethylallyl Diphosphate", J. Am. Chem. Soc. 109, pp. 5544-5545 (1987).

Mookhtiar, K.A. et al., "Heterologous expression and characterization of rat liver gluockinase regulatory protein", Diabetes, 45:1670-1677 (1996).

Murakami, K. et al., "A Novel Insulin Sensitizer Acts as a Coligand for Peroxisome Proliferator-Activated Receptor-α(PPAR-α) and PPAR-γ", Diabetes vol. 47, pp. 1841-1847 (1998).

Nicolosi et al., "The ACAT inhibitor, C1-1011 is effective in the prevention and regression of aortic fatty streak area in hamsters", Atherosclerosis 137(1):77-85 (1998).

Ortiz de Montellano, P. et al., "Inhibition of Squalene Synthetase by Farnesyl Pyrophosphate Analogues", J. Med. Chem., 20:243-249 (1977).

Remington's Pharmaceutical Sciences, 17th ed., Mack Publishing Co., Easton, PA, p. 1418 (1985).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem. 41, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-diphenylimidazole ACAT Inhibitor", Bioorganic & Med. Chem. Lett., vol. 6, No. 1, pp. 47-50, (1996).

Sorbera, L.A. et al., "Treatment of Lipoprotein Disorders ACAT Inhibitor", Drugs of the Future, 24(1), pp. 9-15 (1999).

Suaifen et al., "Effects of steric bulk and stereochemistry on the rates of diketopiperazine formation from N-aminoacyl-2,2-dimethylthiazolidine-4-carboxamide (Dmt dipeptide amides)—a model for a new prodrug linker system", Tetrahedron, 62:11245-11266 (2006).

Wermuth, C.G., et al., The Practice of Medicinal Chemistry, Chapter 31, (Academic Press) 1996.

Yamada, M. et al., "A Potent Dipeptide Inhibitor of Dipeptidyl Peptidase IV", Biorganic & Med. Chem. Lett. 8, pp. 1537-1540 (1998).

* cited by examiner

GLUCOKINASE ACTIVATORS AND METHODS OF USING SAME

FIELD OF THE INVENTION

The present invention relates to novel amide compounds which are activators of the enzyme glucokinase and thus are useful in treating diabetes, and to a method for treating diabetes, especially Type II diabetes, using such compounds.

BACKGROUND OF THE INVENTION

The enzyme glucokinase (UK), which is mainly found in pancreatic β-cells and liver parenchymal cells, catalyzes the conversion of glucose to glucose-6-phosphate, which is the first step in the metabolism of glucose. Glucokinase is also a rate-controlling enzyme for glucose metabolism in pancreatic β-cells and liver parenchymal cells, which play an important role in whole-body glucose homeostasis.

Liag, Y. et al., (*Biochem. J.*, 309:167-173 (1995)) report the finding that Type II (maturity-onset) diabetes of the young (MODY-2) is caused by loss of function mutations in the glucokinase gene, which suggests that glucokinase also functions as a glucose sensor in humans. Thus, compounds that activate glucokinase and thus increase the sensitivity of the glucokinase sensor system and thereby cause increase in insulin secretion will be useful in the treatment of hyperglycemia and Type II diabetes.

Glucokinase activators have been demonstrated to be effective in enhancing: 1) the effect of glucose on insulin release from isolated rat and human pancreatic islets, and 2) the glucose induction of pancreatic islet glucokinase in isolated cultured rat islets (e.g., Matschinsky, F. M. et al., *Diabetes*, 55:1 (2006), and Matschinsky, F. M. et al., eds., *Glucokinase and Glycemic Disease, from Basics to Novel Therapeutics*, Karger, publ., Ch. 6, pp. 360-378 (2004)). In diabetic animal model studies, glucokinase activators have been demonstrated to stimulate insulin release, enhance glycogen synthesis and reduce hepatic glucose production in pancreatic clamp studies. Importantly, glucokinase activators have been demonstrated to dose-dependently lower blood glucose levels in different standard animal models of type 2 diabetes, such as the ob/ob mouse, db/db mouse and Zucker fa/fa rat in acute single-dose studies and also effectively improved the glucose excursion in both normal C57/BL6J and ob/ob mice in oral glucose tolerance tests (e.g., in Matschinsky, F. M. et al., eds., *Glucokinase and Glycemic Disease, from Basics to Novel Therapeutics*, Karger, publ., Ch. 6, pp. 360-378 (2004) as well as Fyfe, M. C. et al., *Diabetologia*, 50:1277 (2007)).

Glucokinase activators have also demonstrated antidiabetic efficacy in chronic animal models of type II diabetes. For instance, in a 9-day study in ob/ob mice, a glucokinase activator improved the overall glucose profile while showing comparable antihyperglycemic effects in oral glucose tolerance tests at the beginning and end of the study (Fyfe, M. C. et al., *Diabetologia*, 50:1277 (2007)). In another instance, in a chronic 40-week study, a glucokinase activator prevented the development of hyperglycemia in diet-induced obese mice which were glucose intolerant. The diet-induced obese mice treated with a glucokinase activator showed marked improvement in the glucose excursion in an oral glucose tolerance test at the end of the study relative to the control group (Matschinsky, F. M. et al., eds., *Glucokinase and Glycemic Disease, from Basics to Novel Therapeutics*, Karger, publ., Ch. 6, pp. 360-378 (2004).

SUMMARY OF THE INVENTION

In accordance with one aspect of the invention, compounds are provided having the structure I

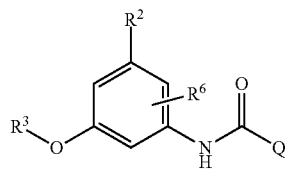

where Q is

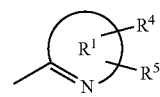

Or
Q is —C(O)NR$^7$R$^8$,
that is

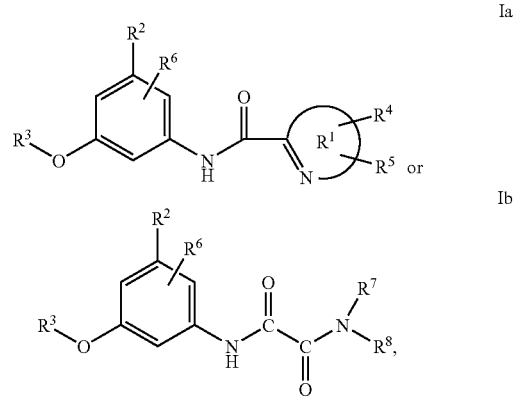

respectively,
or a pharmaceutically acceptable salt thereof, a prodrug ester thereof, and all stereoisomers thereof, including enantiomers and diastereomers thereof;

wherein the R$^1$ ring is a heteroaryl ring, monocyclic (5- or 6-membered ring) or bicyclic (all possible combinations of 5 and 6 membered rings), containing a nitrogen atom adjacent to the carbonyl linked ring carbon and possessing optionally 1 to 5 additional heteroatoms selected from N, O and S, and optionally one or two additional substituents independently chosen from R$^4$ and R$^5$ that may be the same or different, and when substituents are attached to a N atom of the ring, a quaternary nitrogen center is not formed;

R$^4$ and R$^5$ are the same or different and are independently selected from H, alkyl, halogen, CN, —C(O)NR$^7$R$^8$, —CO$_2$R$^9$, and -L-M-Q$_a$-;
L is O, S, SO$_2$, NR$^{9a}$ or absent;
M is C$_{1-4}$ alkyl optionally substituted with OH, NH$_2$, or C$_{2-5}$ alkylene, or M is absent;

$Q_a$ is halogen, $-OR^{9b}$, $-NR^7R^8$, $-CO_2H$, $-CO_2R^{9c}$, $-C(O)NR^7R^8$, CN, N-linked amide ($-NR^7C(O)R^8$), N-linked sulfonamide ($-NR^9SO_2R^{10}$), N-linked carbamate ($-NR^8CO_2R^{10}$), O— linked carbamate ($-OCONR^7R^8$), N-linked urea ($-NR^9C(O)NR^7R^8$), and aryl or heteroaryl both optionally substituted with one or groups selected from V;

V is halogen, $-OR^9$, $-NR^7R^8$, $-CO_2H$, $-CO_2R^7$, $-C(O)NR^7R^8$, CN, N-linked amide ($-NR^7COR^8$), N-linked sulfonamide)($-NR^9SO_2R^{10}$), N-linked carbamate ($-NR^8COOR^{10}$), N— linked urea ($-NR^9CONR^7R^8$), or sulfonamide ($-SO_2NR^7R^8$), and the resulting group -L-M-$Q_a$ is not a chemically unstable entity;

$R^6$ is H, OH, $C_{1-6}$ alkyl, halogen, CN, $-C(O)NH_2$ or carboxyl, or $R^6$ is absent;

$R^7$ and $R^8$ (regardless of which group each is a part of) are the same or different and are independently selected from H, alkyl, cycloalkyl, aryl, arylalkyl, heteroaryl, and heteroarylalkyl, or $R^7$ and $R^8$ are cyclized together to form a 3- to 7-membered heterocycle;

$R^9$ and $R^{9c}$ (regardless of which group each is a part of) are independently selected from H, alkyl, aryl, or arylalkyl;

$R^{10}$ (regardless of which group it is a part of) is independently selected from alkyl, aryl, heteroaryl, aralkyl, or heteroarylalkyl;

$R^2$ and $R^3$ are same or different, and are independently selected from Y—Z—;

each —Z— is independently selected from a direct bond, or a linker atom selected from —O—, —N($R^9$)—, —S—, —S(O)—, —S(O)$_2$—, —C(O)—, or a group of the formula —(CH$_2$)$_p$—C(R$^{11}$)$_2$—(CH$_2$)$_q$—;

each Y is independently selected from aryl-$Z^1$—, heteroaryl-$Z^1$, heterocyclyl-$Z^1$—, where the aryl, heteroaryl or heterocyclyl is connected to $Z^1$ through a ring nitrogen or carbon;

or Y is independently selected from $C_{3-7}$cycloalkyl-$Z^1$—, $C_{1-6}$alkyl-$Z^1$—, $C_{2-6}$-alkenyl-$Z^1$—, $C_{2-6}$-alkynyl-$Z^1$—, —$Z^1$—CH(CH$_{3-a}$F$_a$)$_2$, or —$Z^1$—(CH$_2$)$_{0-4}$CH$_{3-a}$F$_a$;

wherein each Y is independently optionally substituted by up to 3 $R^{12}$ groups;

each $R^{12}$ is independently selected from halogen, $-CH_{3-a}F_a$, CN, NO$_2$, NH$_2$, $C_{1-6}$alkyl, OC$_{1-6}$alkyl, —COOH, OH, aryloxy, heteroaryloxy, heterocyclyloxy, —S—$R^{10}$, —S(O)—$R^{10}$, —SO$_2$R$^9$, —SO$_2$NR$^7$R$^8$, —NR$^7$R$^8$, —CO$_2$R$^9$, —C(O)N$^7$R$^8$, N-linked amide (—NR$^7$C(O)R$^8$), N-linked sulfonamide (—NR$^9$SO$_2$R$^{10}$), N-linked carbamate) (—NR$^8$CO$_2$R$^{10}$, O— linked carbamate (—OCONR$^7$R$^8$), N-linked urea (—NR$^9$C(O)NR$^7$R$^8$), —(CH$_2$)$_p$—PO(OR$^7$)(OR$^8$), —(CH$_2$)$_p$—PO(OR$^7$)R$^8$, —(CH$_2$)$_p$—O—PO(OR$^7$)R$^8$, —(CH$_2$)$_p$O—PO—(R$^7$)R$^8$, —(CH$_2$)$_p$—P(O)R$^7$R$^8$, aryl, heteroaryl, or heterocyclyl;

wherein each phenyl, naphthyl, heteroaryl, or heterocyclyl ring in Y or $R^{12}$ is optionally substituted by halogen, =O, =S, $C_{1-6}$alkyl, —CH$_{3-a}$F$_a$, CN, NO$_2$, NH$_2$, —COOH, OH, $C_{1-6}$alkyl, —OC$_{1-6}$alkyl, —C(O)OC$_{1-6}$alkyl, —NR$^{7a}$R$^{8a}$, —C(O)NR$^{7a}$R$^{8a}$, N-linked amide (—NR$^{7a}$COR$^{8a}$), N-linked sulfonamide (—NR$^{9a}$SO$_2$R$^{10a}$), N-linked carbamate (—NR$^{8a}$COOR$^{10a}$), N-linked urea (—NR$^{9a}$CONR$^{7a}$R$^{8a}$), sulfonamide (—SO$_2$NR$^{7a}$R$^{8a}$), —(CH$_2$)$_p$—PO(OR$^{7a}$)(OR$^{8a}$), —(CH$_2$)$_p$—PO(OR$^{7a}$)R$^{8a}$, —(CH$_2$)$_p$—O—PO(OR$^{7a}$)R$^{8a}$, —(CH$_2$)$_p$O—PO—(R$^{7a}$)R$^{8a}$, or —(CH$_2$)$_p$—P(O)R$^{7a}$R$^{8a}$;

each —$Z^1$— is independently selected from a direct bond, or a linker atom selected from —O—, —N($R^9$)—, —S—, —S(O)—, —S(O)$_2$—, —C(O)—, or a group of the formula —(CH$_2$)$_p$—C(R$^{11}$)$_2$—(CH$_2$)$_q$—;

$R^{11}$ is independently selected from hydrogen, $C_{1-6}$alkyl, haloC$_{1-6}$alkyl, or $C_{2-4}$alkyl-O—$C_{1-4}$alkyl;

each a is independently an integer from 1, 2, 3;

p is independently an integer from 0, 1 or 2;

q is independently an integer from 0, 1 or 2;

and p+q<4;

$R^{7a}$ and $R^{8a}$ are the same or different and are independently selected from H, alkyl, cycloalkyl, aryl, arylalkyl, heteroaryl and heteroarylalkyl or $R^{7a}$ and $R^{8a}$ cyclized together to form a 3- to 7-membered heterocyclo;

$R^{9a}$ and $R^{9b}$ are independently selected from H, alkyl, aryl, heterocyclyl, aralkyl, or heteroarylalkyl; and $R^{10a}$ is independently selected from alkyl, aryl, heteroaryl, aralkyl or heteroarylalkyl.

By the term "independently selected from" refers to the use of the same variable or substituent designation more than once in the same molecule and each such use is independent of each other, for example, (1) Y—Z, used more than once in the same molecule such as in defining $R^2$ and $R^3$, wherein Y—Z— with respect to $R^2$ may be same as or different from and is independent from Y—Z— defined with respect to $R^3$;

or (2) $R^7$ and/or $R^8$ used more than once in the same molecule;

or (3) $R^9$ and/or $R^{10}$ used more than once in the same molecule.

Preferably, in the compounds of formula I,

Q contains an $R^1$ ring which is an N-containing 5- or 6-membered monocyclic heteroaryl ring which optionally contains 1, 2 or 3 additional heteroatoms, which is oxygen, sulfur and/or nitrogen or Q contains an $R^1$ ring which is an N-containing 8-, 9- or 10-membered bicyclic heteroaryl which optionally contains 1, 2 or 3 additional heteroatoms, which is oxygen, sulfur and/or nitrogen;

or Q is

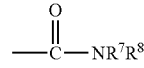

which preferably is

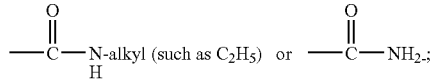

and $R^4$ and $R^5$ are the same or different and are preferably independently selected from H, alkyl, arylalkyl, alkoxycarbonyl or carboxyl.

Examples of preferred Q heteroaryl rings include, but are not limited to

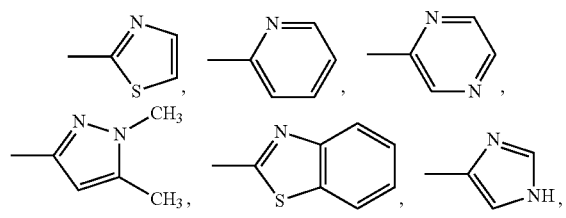

-continued

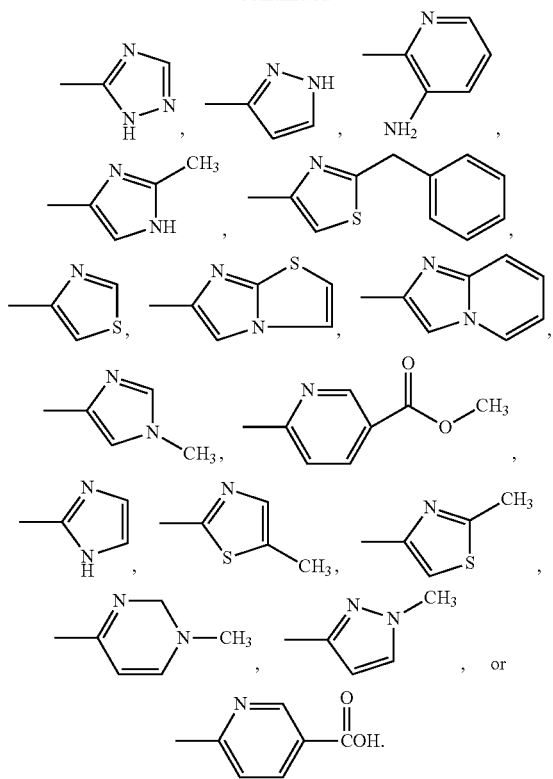

$R^2$ is preferably Y—Z— where
Z is preferably O or a bond; and
Y is $C_{1-6}$alkyl-$Z^1$— where $Z^1$ is a bond,
  aryl-$Z^1$— where $Z^1$ is a bond,
  heterocyclyl-$Z^1$— where $Z^1$ is a bond, or
  heteroaryl-$Z^1$— where $Z^1$ is a bond.

Examples of preferred $R^2$ groups include, but are not limited to,

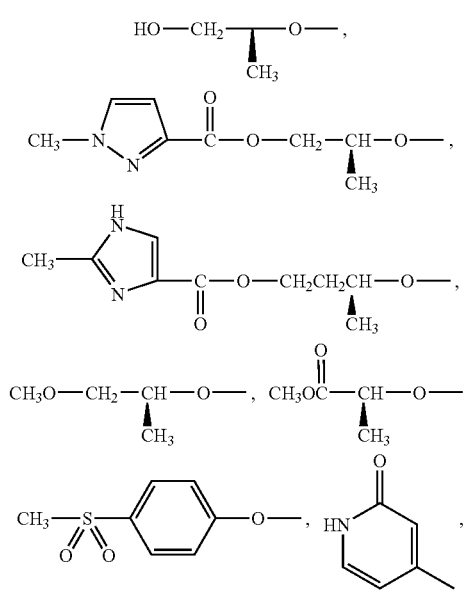

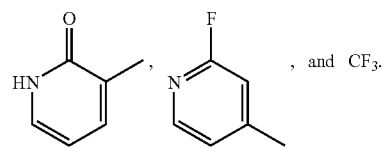

$R^3$ is preferably Y—Z— where Z is a bond, and
Y is aryl$Z^1$ where $Z^1$ is O, and preferably is
$R^6$ is preferably H.

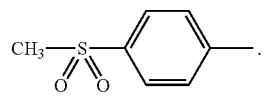

More preferred are compounds of formula I where
$R^1$ is

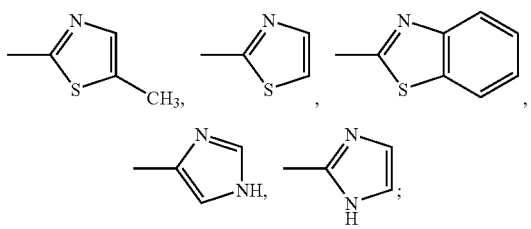

$R^2$ is

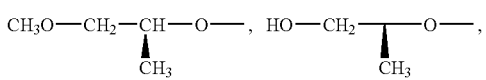

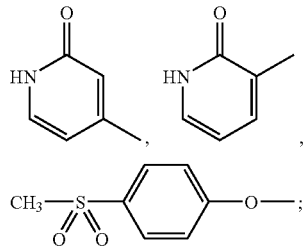

and
$R^3$ is

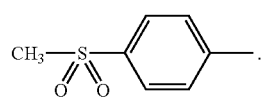

Examples of preferred compounds in accordance with the present invention, include, but are not limited to the following:

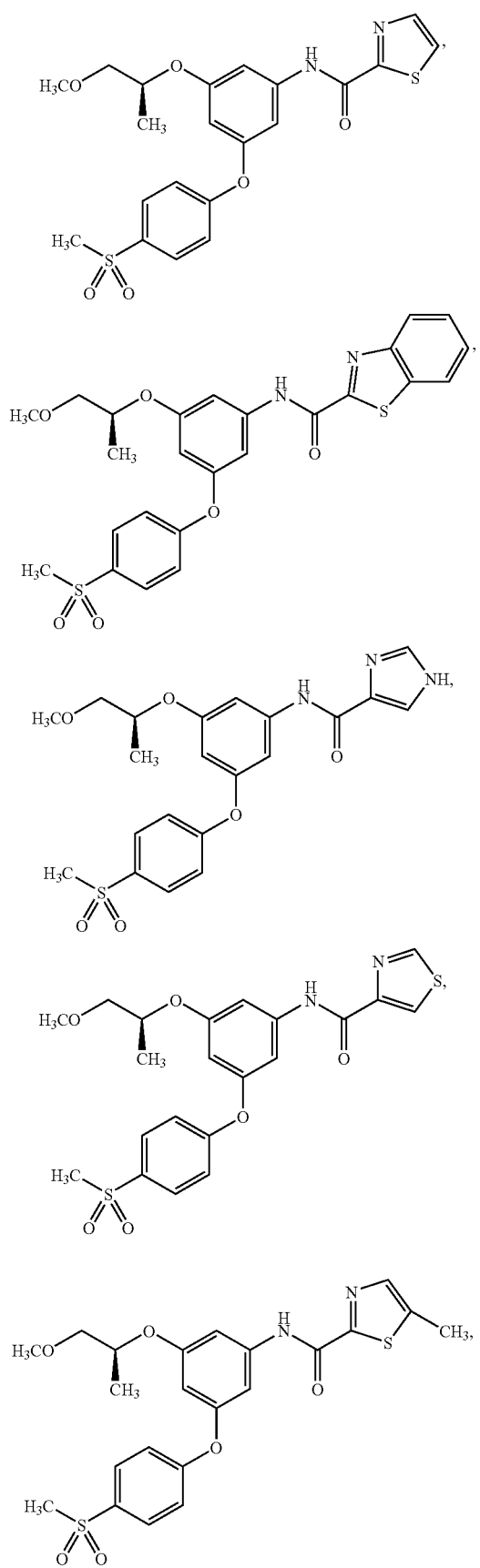
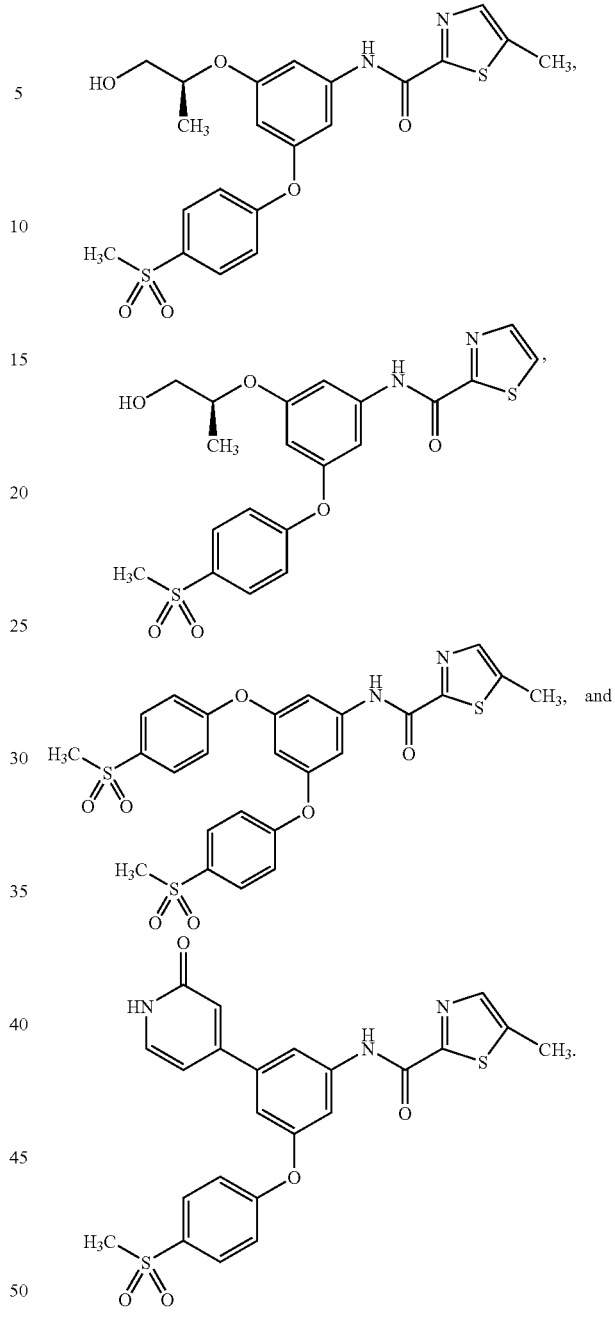

The compounds of the present invention activate or enhance the activity of the enzyme glucokinase. Consequently, the compounds of the present invention may be used in the treatment of multiple diseases or disorders associated with a deficit of glucokinase, such as diabetes and related conditions, microvascular complications associated with diabetes, the macrovascular complications associated with diabetes, cardiovascular diseases, Metabolic Syndrome and its component conditions, and other maladies. Examples of diseases or disorders associated with deficit in activity of the enzyme glucokinase that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

The present invention provides for compounds of formula I, pharmaceutical compositions employing such compounds, and for methods of using such compounds. In particular, the present invention provides a pharmaceutical composition containing a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with deficit in the activity of the enzyme glucokinase, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other therapeutic agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

In another embodiment, compounds of the present invention are selected from the compounds exemplified in the examples.

In another embodiment, the present invention relates to pharmaceutical compositions which include of a therapeutically effective amount of a compound of the present invention, alone or, optionally, in combination with a pharmaceutically acceptable carrier and/or one or more other agent(s).

In another embodiment, the present invention relates to methods of enhancing the activity of the enzyme glucokinase which includes the step of administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with deficit in the activity of the enzyme glucokinase which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the deficit in activity of the enzyme glucokinase that can be prevented, inhibited, or treated according to the present invention include, but are not limited to, are those diseases or disorders set out above.

In another embodiment, the present invention relates to a method for preventing, inhibiting, or treating the progression or onset of diabetes, hyperglycemia, obesity, dyslipidemia, hypertension, and cognitive impairment which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dyslipidemia, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

DETAILED DESCRIPTION OF THE INVENTION

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms, and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^7$ and/or $R^8$) occurs more than one time in any constituent or formula for a compound, its definition at each occurrence is independent of its definition at every other occurrence. Thus, for example, if a group is shown to be substituted with 0-2 $R^7$ and/or $R^8$, then said group may optionally be substituted with up to two $R^7$ and/or $R^8$ groups and $R^7$ and/or $R^8$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Unless otherwise indicated, the term "lower alkyl," "alkyl," or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_a$, $SR_a$, (=S), $-NR_aR_b$, $-N(alkyl)_3^+$, $-NR_aSO_2$, $-NR_aSO_2R_c$, $-SO_2R_c$, $SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}$alkylene)$NR_aR_b$, $-C(=O)NR_a(SO_2)R_b$, $-CO_2(C_{1-4}$alkylene)$NR_aR_b$, $-NR_aC(=O)R_b$, $-NR_aCO_2R_b$, $-NR_a(C_{1-4}$alkylene)$CO_2R_b$, =N—OH, =N—O-alkyl, wherein $R_a$ and $R_b$ are the same or different and are independently selected from hydrogen, alkyl, alkenyl, $CO_2H$, $CO_2$(alkyl), $C_{3-7}$cycloalkyl, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of $(C_{1-6})$alkyl, $(C_{2-6})$alkenyl, hydroxy, halogen, cyano, nitro, $CF_3$, $O(C_{1-6}$ alkyl), $OCF_3$, $C(=O)H$, $C(=O)(C_{1-6}$alkyl), $CO_2H$, $CO_2(C_{1-6}$alkyl), $NHCO_2(C_{1-6}$alkyl), $-S(C_{1-6}$alkyl), $-NH_2$, $NH(C_{1-6}$alkyl), $N(C_{1-6}$alkyl)$_2$, $N(CH_3)_3^+$, $SO_2(C_{1-6}$alkyl), $C(=O)$ $(C_{1-4}$alkylene)$NH_2$, $C(=O)(C_{1-4}$alkylene)NH(alkyl), $C(=O)(C_{1-4}$alkylene)$N(C_{1-4}$alkyl)$_2$, $C_{3-7}$cycloalkyl, phenyl, benzyl, phenylethyl, phenyloxy, benzyloxy, naphthyl, a four to seven membered heterocyclo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclohexyl and cyclododecyl, cyclohexenyl,

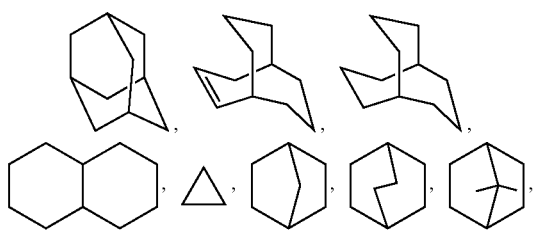

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio, and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

Unless otherwise indicated, the term "aryl" as employed herein alone or as part of another group refers to monocyclic and bicyclic aromatic groups containing 6 to 10 carbons in the ring portion (such as phenyl, biphenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings)

for example

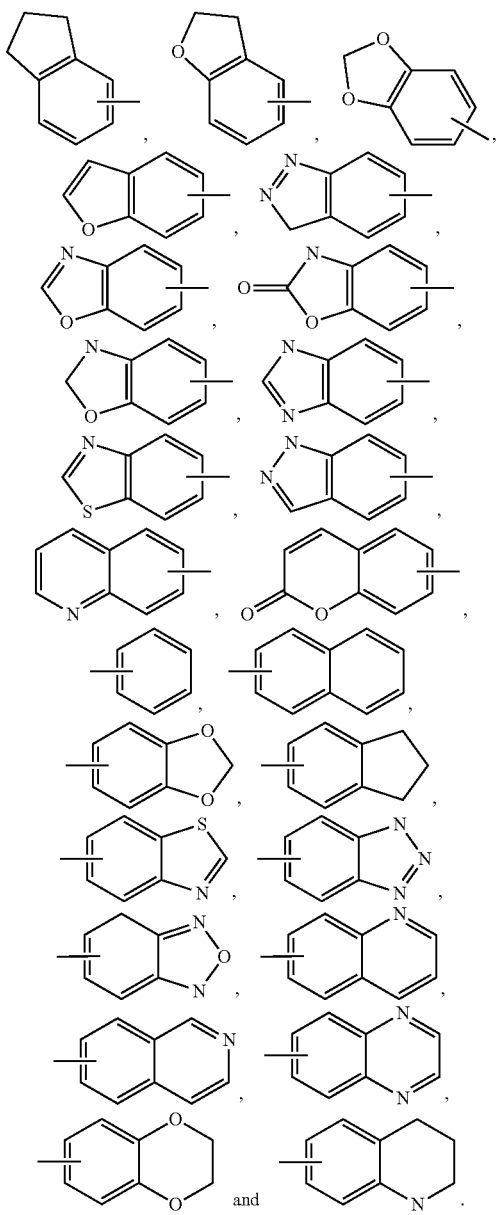

The aryl group may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfon-aminocarbonyl, $OR_a$, $SR_a$, (=S), —$NR_aR_b$, —N(alkyl)$_3^+$, —$NR_aSO_2$, —$NR_aSO_2R_c$, —$SO_2R_c$—$SO_2NR_aR_b$, —$SO_2NR_aC$(=O)$R_b$, $SO_3H$, —PO (OH)$_2$, —C(=O)$R_a$, —CO$_2R_a$, —C(=O)$NR_aR_b$, —C(=O)(C$_{1-4}$alkylene)$NR_aR_b$, —C(=O)$NR_a(SO_2)R_b$, —CO$_2$(C$_{1-4}$alkylene)$NR_aR_b$, —$NR_aC$(=O)$R_b$, —$NR_aCO_2R_b$, or —$NR_a$(C$_{1-4}$alkylene)CO$_2R_b$, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of (C$_{1-4}$)alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), and/or C(=O)(C$_{1-4}$alkylene)N(C$_{1-4}$alkyl)$_2$.and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R_3$ groups or substituents for $R_3$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

The term "acyl" alone or as part of another group refers to a carbonyl group linked to an organic radical, more particularly, the group C(=O)R$_e$, as well as the bivalent groups —C(=O)— or —C(=O)R$_e$—, which are linked to organic radicals. The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The term "heterocyclo" or "heterocyclic" or "heterocyclyl" or "cycloheteroalkyl" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N) (also referred to as cycloheteroalkyl or heterocycloalkyl). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, —SO$_2$NR$_a$C(=O) R$_b$, SO$_3$H, —PO(OH)$_2$, —C(=O)R$_a$, —CO$_2$R$_a$, —C(=O) NR$_a$R$_b$, —C(=O)(C$_{1-4}$alkylene)NR$_a$R$_b$, —C(=O)NR$_a$ (SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$, and R$_c$ are as defined above for substituted alkyl groups, and are also in turn optionally substituted as recited above. When a heterocyclo is substituted with a further ring, said ring in turn is optionally substituted with one to two of (C$_{1-4}$)alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$ alkyl), —S(C$_{1-4}$alkyl), —NH$_2$, NH(C$_{1-4}$alkyl), N(C$_{1-4}$ alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), and/or C(=O) (C$_{1-4}$alkylene)N(C$_{1-4}$alkyl)$_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like. Exemplary bicyclic heterocyclo groups include quinuclidinyl.

Preferred heterocyclo groups in compounds of formula (I) include

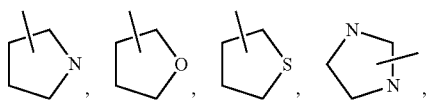

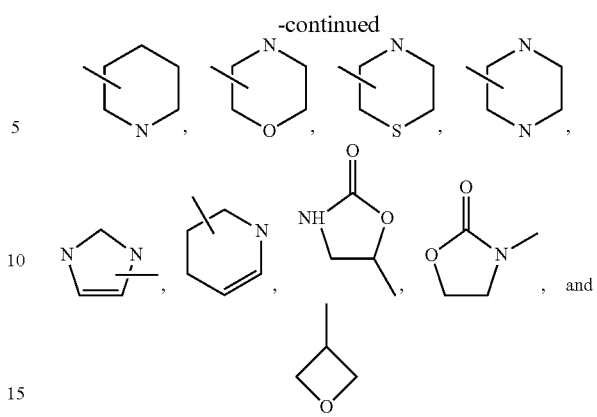

which optionally may be substituted.

The term "heteroaryl" alone or as part of another group refers to substituted and unsubstituted aromatic 5- or 6-membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated, and may include aryl, cycloalkyl, heteroaryl or cycloheteroaryl. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents which may be any of the substituents set out for alkyl and can be selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O) R$_b$, SO$_3$H, —PO(OH)$_2$, —C(=O)R$_a$, —CO$_2$R$_a$, —C(=O) NR$_a$R$_b$, —C(=O)(C$_{1-4}$alkylene)NR$_a$R$_b$, —C(=O)NR$_a$ (SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above. When a heteroaryl is substituted with a further ring, said ring in turn is optionally substituted with one to two of (C$_{1-4}$)alkyl, (C$_{2-4}$)alkenyl, halogen, hydroxy, cyano, nitro, CF$_3$, O(C$_{1-4}$ alkyl), OCF$_3$, C(=O)H, C(=O)(C$_{1-4}$alkyl), CO$_2$H, CO$_2$ (C$_{1-4}$ alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$ alkyl), C(=O)(C$_{1-4}$alkylene)NH$_2$, C(=O)(C$_{1-4}$alkylene)NH (alkyl), and/or C(=O)(C$_{1-4}$alkylene)N(C$_{1-4}$alkyl)$_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, (uranyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

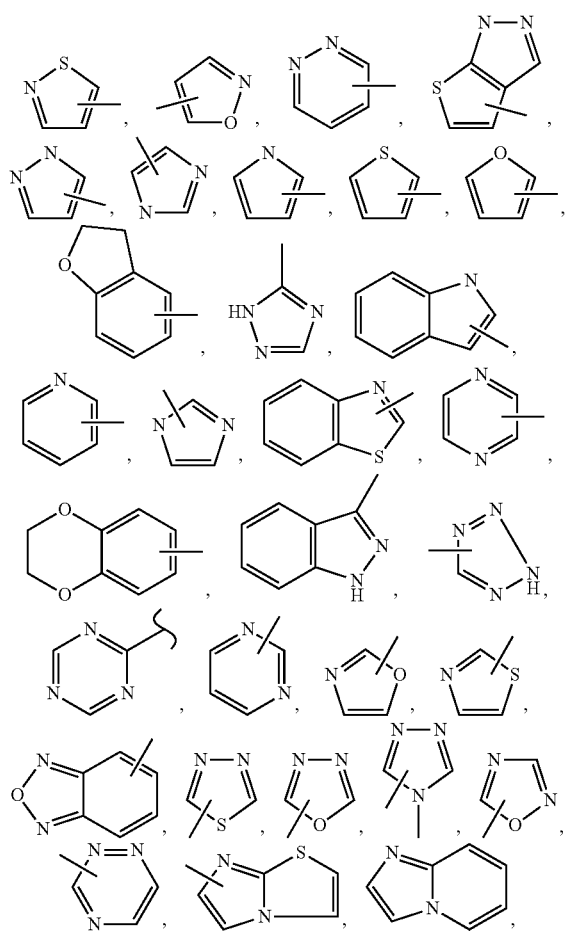

and the like.

The term "heterocyclylalkyl" or "heterocycloalkyl" or "cycloheteroalkylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an —OH group.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

The terms pharmaceutically acceptable "salt" and "salts" may refer to basic salts formed with inorganic and organic bases. Such salts include ammonium salts; alkali metal salts, such as lithium, sodium, and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine, and the like; and zwitterions, the so-called "inner salts." Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid, or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic, or terephthalic acid, such as hydroxycarboxylic acids, for example ascorbic, glycolic, lactic, malic, tartaric, or citric acid, such as amino acids, (for example aspartic or glutamic acid or lysine or arginine), or benzoic acid, or with organic sulfonic acids, such as ($C_1$-$C_4$) alkyl or arylsulfonic acids, which are unsubstituted or substituted, for example by halogen, for example methanesulfonic acid or p-toluenesulfonic acid.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

Any compound that can be converted in vivo to provide the bioactive agent (i.e., the compound of formula I) is a prodrug within the scope and spirit of the invention.

The term "prodrug" denotes a compound which, upon administration to a subject, undergoes chemical conversion by metabolic or chemical processes to yield a compound of the formula, and/or a salt and/or solvate thereof. For example, compounds containing a carboxy group can form physiologically hydrolyzable esters which serve as prodrugs by being hydrolyzed in the body to yield formula compounds per se. Such prodrugs are preferably administered orally since hydrolysis in many instances occurs principally under the influence of the digestive enzymes. Parenteral administration may be used where the ester per se is active, or in those instances where hydrolysis occurs in the blood.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry,* Camille G. Wermuth et al., Ch. 31 (Academic Press, 1996);

b) *Design of Prodrugs,* edited by H. Bundgaard (Elsevier, 1985);

c) *A Textbook of Drug Design and Development,* P. Krogsgaard-Larson and H. Bundgaard, eds. Ch. 5, pp. 113-191 (Harwood Academic Publishers, 1991); and d) *Hydrolysis in Drug and Prodrug Metabolism,* Bernard Testa and Joachim M. Mayer, (Wiley-VCH, 2003).

Said references are incorporated herein by reference.

Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl, or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl, and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as

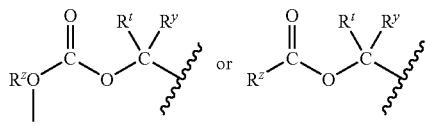

wherein $R^z$, $R^t$, and $R^y$ are H, alkyl, aryl, or arylalkyl; however, $R^zO$ cannot be HO.

Examples of such prodrug esters include

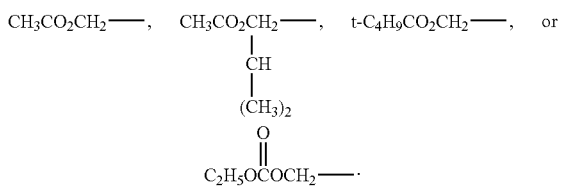

Other examples of suitable prodrug esters include

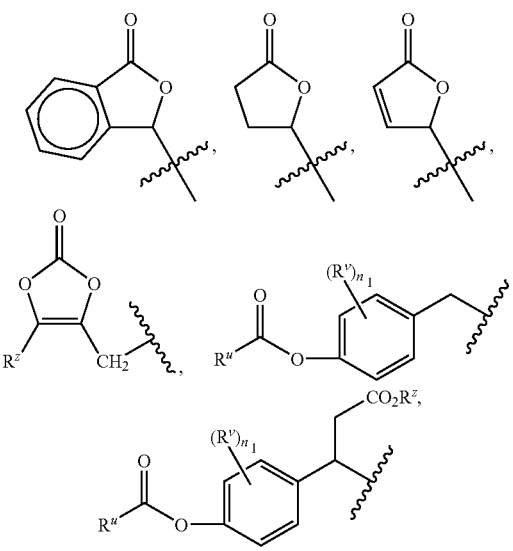

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl, or alkoxyl, and $n_1$ is 0, 1, or 2.

The term "tautomer" refers to compounds of the formula I and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to treat or prevent diabetes and/or obesity.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

Synthesis

Compounds of formulae Ia and Ib may be prepared as shown in the following reaction schemes and the description thereof, as well as relevant literature procedures that may be used by one skilled in the art. Exemplary reagents and procedures for these reactions appear hereinafter and in the working Examples. Protection and deprotection in the Schemes below may be carried out by procedures generally known in the art (see, for example, Greene, T. W. et al., *Protecting Groups in Organic Synthesis*, 3$^{rd}$ Edition, Wiley, publ. (1999)).

Several different methods of synthesis of amide compounds of formula Ia

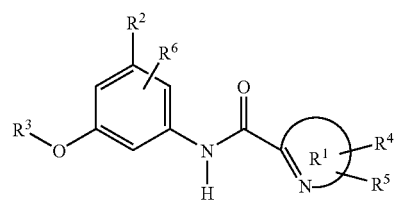

are described in Scheme 1. The arylamine II is coupled with heteroaromatic acid chloride IIIa in presence of an amine base (the acid chloride is generated using standard literature conditions, such as treatment of acid IIIb with oxalyl chloride and a catalytic amount of DMF). Alternatively, treatment of carboxylic acid IIIb with cyanuric fluoride provides the intermediate acid fluoride IIIc, which is reacted with arylamine II in the presence of an amine base (Suaifan et al., *Tetrahedron*, 62:11245-11266 (2006)) to give amide Ia. Finally, a mixture of arylamine II and heteroaromatic acid IIIb can be reacted using standard amide coupling procedures such as BOP/Et$_3$N, EDCI/HOAt/Et$_3$N, or DEPBT (Li et al., *Org. Lett.*, 1:91 (1999)) to directly give amide Ia. Within the heteroaromatic ring R$_1$ and arylamine II depicted in Scheme 1 and in all subsequent schemes described below, the ring substituents R$^4$, R$^5$ and R$^6$ may be optionally present.

Scheme 1

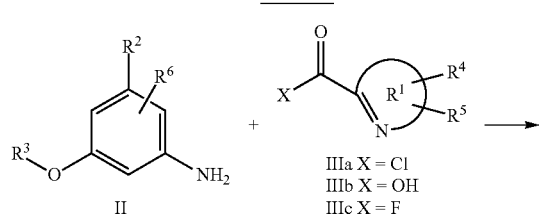

IIIa X = Cl
IIIb X = OH
IIIc X = F

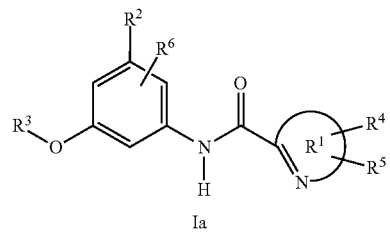

The synthesis of amide compounds of formula Ib

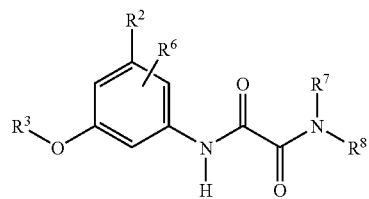

is described in Scheme 2. The arylamine II is coupled with ethyl chlorooxoacetate 2a in the presence of a tertiary amine base (e.g., triethylamine) to give ethyl ester 2b. Subsequent treatment of 2b with an amine (e.g., HNR$^7$R$^8$) affords Ib.

Scheme 2

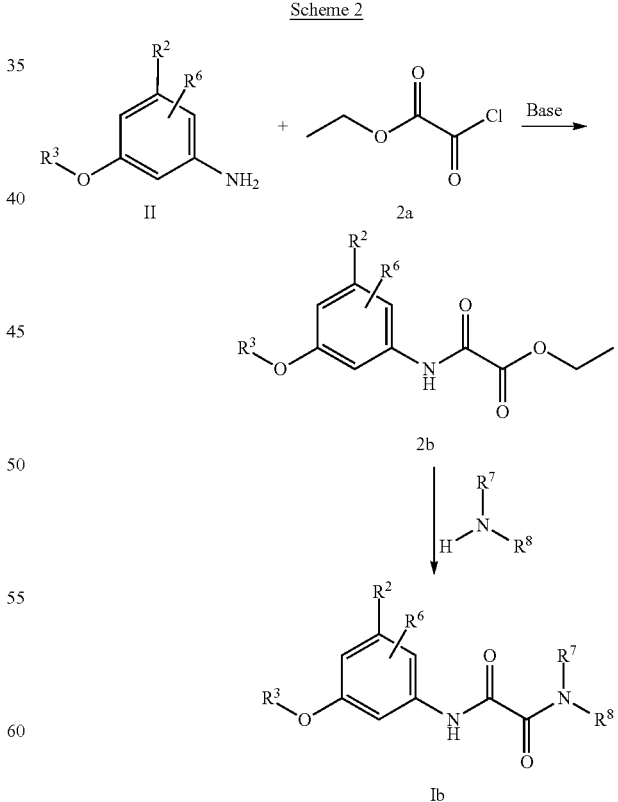

The arylamine II and acid chloride IIIa or carboxylic acid IIIb are either commercially available or can be prepared according to standard literature procedures.

Scheme 3 depicts a general method to synthesize substituted arylamine IIa.

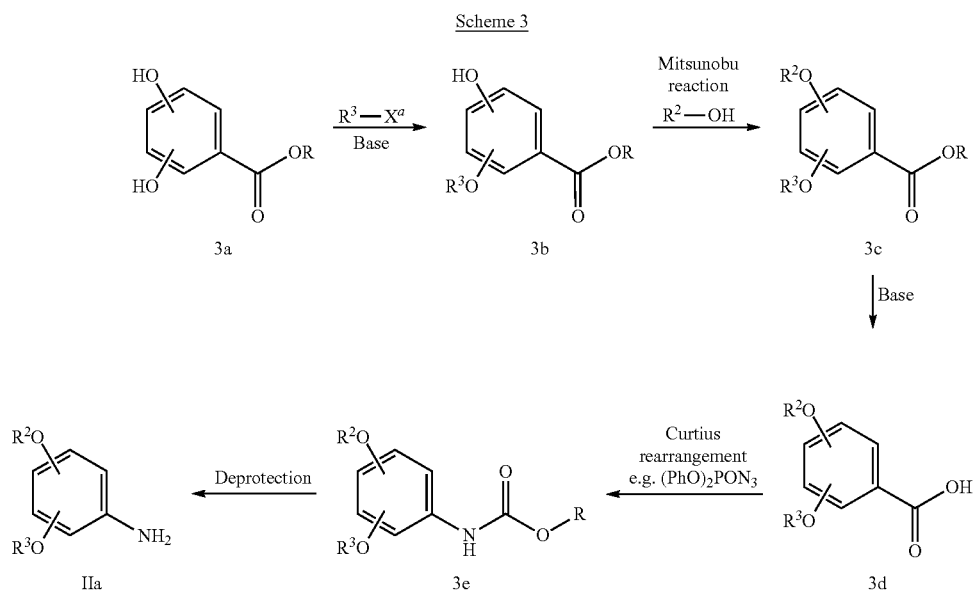

Scheme 3

Alkylation of bis-phenol 3a with an alkyl halide $R^3$—$X^a$ (where $X^a$=Cl or Br, or I) in the presence of a base (e.g., $K_2CO_3$, $Cs_2CO_3$) provides mono-alkylated bis-phenol 3b. Mitsunobu reaction (e.g., diisopropylazodicarboxylate (DIAD) and $PPh_3$) of phenol 3b with an alcohol $R^2$—OH affords the unsymmetrical bis-alkylated phenol 3c. Compound 3c is treated with a base (e.g., aqueous NaOH or LiOH) to give carboxylic acid 3d. Curtius rearrangement of acid 3d under standard conditions (e.g., $(PhO)_2PON_3$ in the presence of an alcohol R—OH, where R=alkyl or arylalkyl) provides carbamate 3e, which is converted to arylamine IIa by either hydrogenation (when R=Bn) or a base (e.g., NaOH, where R=alkyl).

Alternatively, bis-phenol 3a can be symmetrically bis-alkylated with $R^3$—$X^a$ to afford benzoate ester 3c where $R^2$=$R^3$. Further transformation according to Scheme 2 provides symmetrical substituted phenyl amine IIa where $R^2$=$R^3$.

As shown in Scheme 4, when necessary, phenol 3b can be protected (e.g., TBDPSCl/imidazole, as the TBDPS ether, or $BnBr/K_2CO_3$, as the benzyl ether, etc.) to provide 4c, which is converted to the substituted arylamine IIb via the same sequence previously described to convert 3c to IIa in Scheme 3. A standard coupling reaction (e.g., EDCI/HOBT) between IIb and IIIa or IIIb affords amide 4d. Subsequent deprotection of 4d gives 4e, which can either be alkylated with $R^2$—$X^a$ in the presence of a suitable base (e.g., $K_2CO_3$, $Cs_2CO_3$) or through a Mitsunobu reaction (e.g., DIAD and $PPh_3$) with an alcohol $R^2$—OH to afford alkylated phenol-amide Ic.

Scheme 4

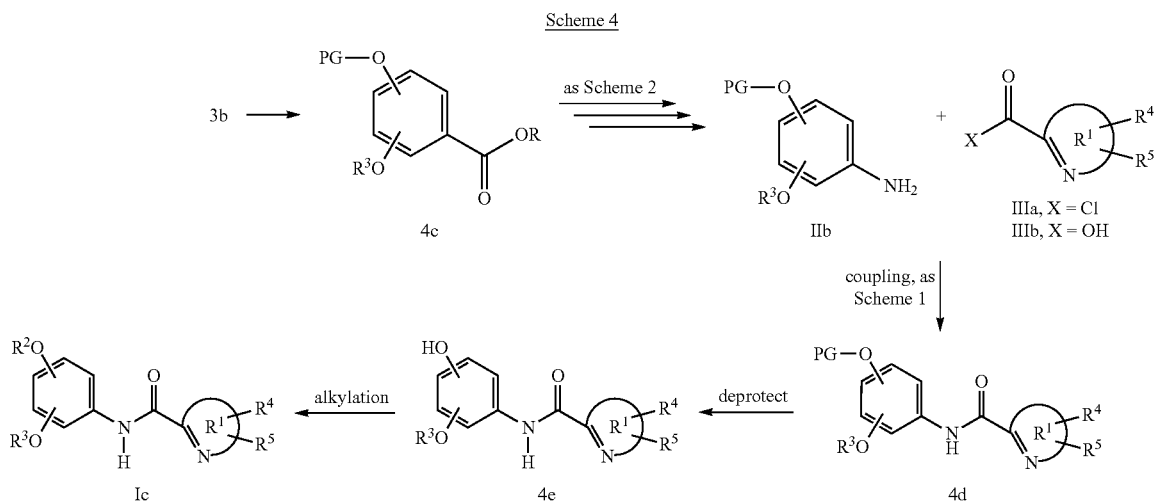

Another general synthetic route for the preparation of substituted arylamine IIc is shown in Scheme 5.

Scheme 5

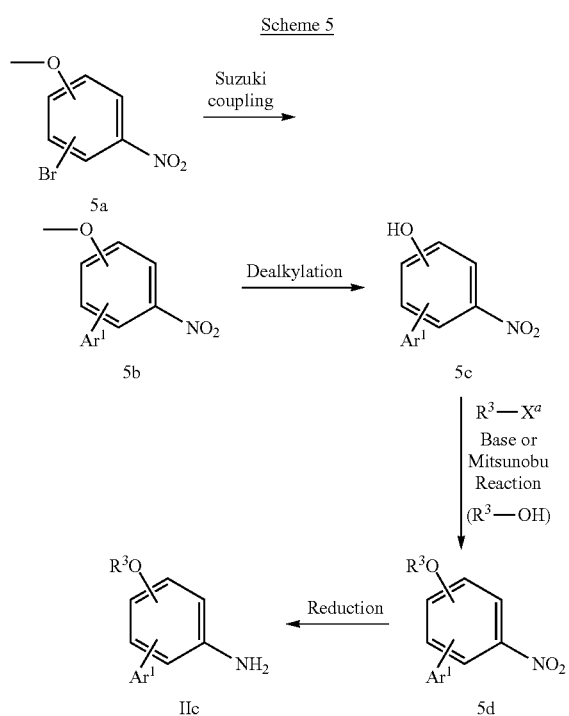

Suzuki coupling reaction (e.g., with Pd(PPh$_3$)$_4$ as catalyst) of bromide 5a with an arylboronic acid provides the biaryl 5b. Dealkylation of the ether with BBr$_3$ affords phenol 5c. Subsequent alkylation of the phenol 5c with R$^3$—X$^a$ in the presence of a base (e.g., K$_2$CO$_3$, Cs$_2$CO$_3$) or via a Mitsunobu reaction (e.g., DIAD and PPh$_3$) of the phenol 5c with the alcohol R$^3$—OH affords 5d, which is readily converted to amine IIc by reduction of the nitro group (e.g., H$_2$/Pd—C, Fe/HOAc).

Scheme 6 shows another synthetic sequence for the preparation of the substituted arylamine IId. Compound 6a is converted to phenol 6b through a nucleophilic substitution reaction (e.g., KOH under microwave conditions). Esterification of 6b provides 6c, which is alkylated at the phenolic oxygen with R$^3$—X in the presence of a base (e.g., K$_2$CO$_3$, Cs$_2$CO$_3$) or via a Mitsunobu reaction (e.g., DIAD and PPh$_3$) of the phenol 6c with an alcohol R$^3$—OH to afford 6d. Suzuki coupling reaction (e.g., Pd(PPh$_3$)$_4$ as catalyst) of 6d with an arylboronic acid R$_2$B(OH)$_2$ provides 6e. Saponification of the methyl ester 6e affords acid 6f, which is further converted to arylamine IId by a Curtius rearrangement reaction through carbamate 6g followed by deprotection (e.g., by hydrogenolysis with H$_2$/Pd).

Scheme 6

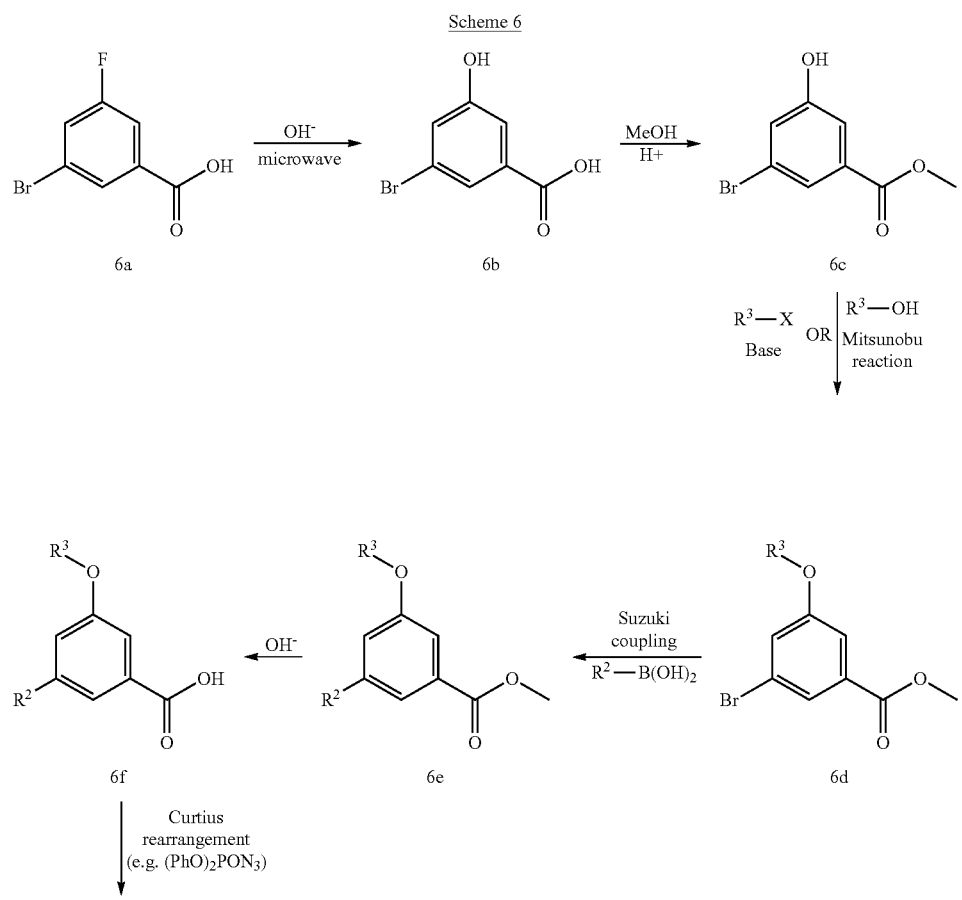

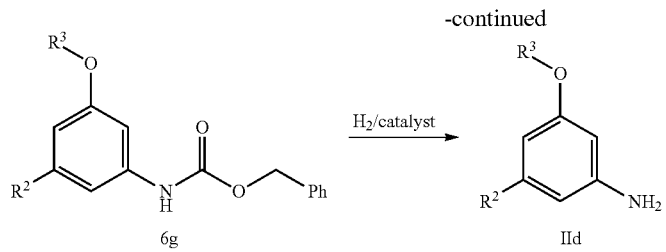

In each of the aforementioned synthetic methods, when the starting material compound or compound I has an amino group, a carboxyl group, a hydroxyl group or a thiol group, a protecting group generally used in peptide chemistry or those generally known in the art (see, for example, Greene, T. W. et al., *Protecting Groups in Organic Synthesis*, 3$^{rd}$ Edition, Wiley, publ. (1999)) may be introduced into these groups. In addition, the protecting group can be removed according to a conventional method in any step of each reaction scheme.

Utilities and Combinations

A. Utilities

The compounds of the present invention possess activity as enhancers of activity of the enzyme glucokinase, and, therefore, may be used in the treatment of diseases associated with glucokinase activity.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

Metabolic Syndrome or "Syndrome X" is described in Ford, et al., *J. Am. Med. Assoc.*, 287:356-359 (2002) and Arbeeny et al., *Curr. Med. Chem.—Imm., Endoc. & Metab. Agents*, 1:1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other enhancers of activity of glucokinase or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-infective agents, anti-ischemic agents, anti-hypertensive agents, anti-obesity agents, anti-dyslipidemic agents, anti-hyperlipidemic agents, anti-hypertrigiyceridemic agents, anti-hypercholesterolemic agents, anti-ischemic agents, anti-cancer agents, anti-cytotoxic agents, anti-restenotic agents, anti-pancreatic agents, lipid lowering agents, appetite suppressants, memory enhancing agents, and cognitive agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones (PPARgamma agonists): ciglitazone, pioglitazone, troglitazone, rosiglitazone; non-thiazolidinedione PPAR-gamma agonists; selective PPARgamma modulators (SPPARMs; e.g., metaglidasen from Metabolex); PPAR-alpha agonists; PPAR alpha/gamma dual agonists; PPAR delta agonists, PPARalpha/gamma/delta pan agonists; SGLT2 inhibitors; dipeptidyl peptidase-IV (DPP4) inhibitors; aldose reductase inhibitors; RXR agonists: JTT-501, MX-6054, DRF2593, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's farglitazar (GI-262570), englitazone (CP-68722, Pfizer), or darglitazone (CP-86325, Pfizer), isaglitazone (MIT/J&J), JTT-501 (JPNT/P&U), L-895645 (Merck), R-119702 (Sankyo/WL), N,N-2344 or balaglitazone (Dr. Reddy/NN), or YM-440 (Yamanouchi).

Suitable PPAR α/γ dual agonists include muraglitazar (Bristol-Myers Squibb), tesaglitazar (Astra/Zeneca), naveglitazar (Lilly/Ligand); AVE-0847 (Sanofi-Aventis); TAK-654 (Takeda), as well as those disclosed by Murakami et al, "A Novel Insulin Sensitizer Acts As a Coligand for Peroxisome Proliferation—Activated Receptor α(PPARα) and PPARγ; Effect of PPARα Activation on Abnormal Lipid Metabolism in Liver of Zucker Fatty Rats", Diabetes, 47:1841-1847 (1998), WO 01/21602 and U.S. Pat. No. 6,414,002, the disclosure of which is incorporated herein by reference, employing dosages as set out therein, which compounds designated as preferred are preferred for use herein. Suitable PPARδ agonists include, for example, GW-501516 (Glaxo). Suitable PPARα/γ/δ pan agonists include, for example, GW-677954 (Glaxo).

Suitable α2 antagonists also include those disclosed in WO 00/59506, employing dosages as set out herein.

Suitable SGLT2 inhibitors include dapagliflozin (Bristol-Myers Squibb), sergiflozin (Glaxo SmithKline), T-1095, phlorizin, WAY-123783, and those described in WO 01/27128.

Suitable DPP4 inhibitors include saxagliptin (Bristol-Myers Squibb), vildagliptin (Novartis) and sitagliptin (Merck) as well as those disclosed in WO 99/38501, WO 99/46272, WO 99/67279 (PROBIODRUG), WO 99/67278 (PROBIO-DRUG), WO 99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al., Biochemistry, 38(36):11597-11603 (1999), TSL-225 (tryptophyl-1,2,3,4-tetrahydroisoquinoline-3-carboxylic acid) as disclosed by Yamada et al., Bioorg. & Med. Chem. Lett., 8:1537-1540 (1998), 2-cyanopyrrolidides and 4-cyanopyrrolidides, as disclosed by Ashworth et al., Bioorg. & Med. Chem. Lett., 6(22):1163-1166 and 2745-2748 (1996), employing dosages as set out in the above references.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) include GLP-1 (1-36) amide, GLP-1(7-36) amide, GLP-1(7-37) (as disclosed in U.S. Pat. No. 5,614,492 to Habener), as well as AC2993 (Amylin), and LY-315902 (Lilly).

Other anti-diabetic agents that can be used in combination with compounds of the invention include ergoset and D-chiroinositol.

Suitable anti-ischemic agents include, but are not limited to, those described in the Physicians' Desk Reference and NHE inhibitors, including those disclosed in WO 99/43663.

Examples of suitable anti-infective agents are antibiotic agents, including, but not limited to, those described in the Physicians' Desk Reference.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, bile acid sequestrants, cholesterol ester transfer protein inhibitors (e.g., torcetrapib (Pfizer)), and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983, and 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929, and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440; and related statin compounds disclosed in U.S. Pat. No. 5,753,675; pyrazole analogs of mevalonolactone derivatives, as disclosed in U.S. Pat. No. 4,613,610; indene analogs of mevalonolactone derivatives, as disclosed in PCT application WO 86/03488; 6-[2-(substituted-pyrrol-1-yl)alkyl)pyran-2-ones and derivatives thereof, as disclosed in U.S. Pat. No. 4,647,576; Searle's SC-45355 (a 3-substituted pentanedioic acid derivative) dichloroacetate; imidazole analogs of mevalonolactone, as disclosed in PCT application WO 86/07054; 3-carboxy-2-hydroxy-propane-phosphonic acid derivatives, as disclosed in French Patent No. 2,596,393; 2,3-disubstituted pyrrole, furan and thiophene derivatives, as disclosed in European Patent Application No. 0221025; naphthyl analogs of mevalonolactone, as disclosed in U.S. Pat. No. 4,686,237; octahydronaphthalenes, such as disclosed in U.S. Pat. No. 4,499,289; keto analogs of mevinolin (lovastatin), as disclosed in European Patent Application No. 0142146 A2; and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin, and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al., J. Med. Chem., 31(10):1869-1871 (1988), including isoprenoid (phosphinyl-methyl)phosphonates, as well as other known squalene synthetase inhibitors, for example, as disclosed in U.S. Pat. Nos. 4,871,721 and 4,924,024 and in Biller, S. A. et al., Current Pharmaceutical Design, 2:1-40 (1996).

In addition, other squalene synthetase inhibitors suitable for use herein include the terpenoid pyrophosphates disclosed by Ortiz de Montellano, P. et al, J. Med. Chem., 20:243-249 (1977), the farnesyl diphosphate analog A and presqualene pyrophosphate (PSQ-PP) analogs as disclosed by Corey et al., J. Am. Chem. Soc., 98:1291-1293 (1976), phosphinylphosphonates reported by McClard, R. W. et al, J. Am. Chem. Soc., 109:5544 (1987) and cyclopropanes reported by Capson, T. L., Ph.D., dissertation, June 1987, Dept. Med. Chem. U. of Utah, Abstract, Table of Contents, pp. 16, 17, 40-43, 48-51, Summary.

The fibric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in *Drugs of the Future*, 24:9-15 (1999), (Avasimibe); Nicolosi et al, "The ACAT inhibitor, Cl-1011 is effective in the prevention and regression of aortic fatty streak area in hamsters", *Atherosclerosis*, (Shannon, Irel.), 137(1): 77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause, B. R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R. R. et al., eds., pp. 173-198 (1995); Sliskovic et al., "ACAT inhibitors: potential anti-atherosclerotic agents", *Curr. Med. Chem.*, 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl] ureas with enhanced hypocholesterolemic activity", *Chemtracts: Org. Chem.*, 8(6):359-362 (1995), or TS-962 (Taisho Pharmaceutical Co. Ltd.).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitors for use in combination with the compounds of the invention include SCH48461 (Schering-Plough), as well as those disclosed in *Atherosclerosis*, 115:45-63 (1995) and *J. Med. Chem.*, 41:973 (1998).

Examples of suitable ileal Na+/bile acid cotransporter inhibitors for use in combination with the compounds of the invention include compounds as disclosed in *Drugs of the Future*, 24:425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999).

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, and those discussed in Hertzog, D. L., *Expert Opin. Ther. Patents*, 14:1435-1452 (2004).

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983, and 5,488,064, with AJ9677, L750, 355, and CP331648 being preferred.

Examples of lipase inhibitors which may be optionally employed in combination with compounds of the present invention include orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson), or axokine (Regeneron), with sibutramine and topiramate being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., HP-228); leptin or mimentics; 11-beta-hydroxysteroid dehydrogenase type-1 inhibitors; urocortin mimetics, CRF antagonists, and CRF binding proteins (e.g., RU-486, urocortin).

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as eeteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators; and monoclonal antibodies. Additional anti-cancer agents are disclosed in EP 1177791. The compounds of the invention may also be used in conjunction with radiation therapy.

Examples of suitable memory enhancing agents, anti-dementia agents, or cognitive agents for use in combination with the compounds of the present invention include, but are not limited to, donepezil, rivastigmine, galantamine, memantine, tacrine, metrifonate, muscarine, xanomelline, deprenyl, and physostigmine.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules, or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules, or powders. The dose for adults is between 0.5 and 2,000 mg per day, preferably between 1 and 500 mg, which can be administered in a single dose or in the form of individual doses from 1-4 times per day.

A typical capsule for oral administration contains compounds of structure (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

EXAMPLES

The following working Examples serve to better illustrate, but not limit, some of the preferred embodiments of the present invention.

General

The term HPLC refers to an analytical Shimadzu high performance liquid chromatograph using one of following methods:

Method A: YMC or Phenomenex C18 5 μm 4.6×50 mm column; 4 min continuous gradient from 0 to 100%, then hold at 100% solvent B for 1 minute; where A=10% MeOH:90% $H_2O$:0.2% $H_3PO_4$ and B=90% MeOH:10% $H_2O$:0.2% $H_3PO_4$; flow rate=4 mL/min, UV detection at 220 mm Method B: Zorbax SB C18 5 μm 4.6×75 mm column; 8 min continuous gradient of 50% solvent A:B to 100% B, then hold at 100% solvent B for 2 minute; where A=10% MeOH+90% $H_2O$+0.2% $H_3PO_4$, and B=90% MeOH+10% $H_2O$+0.2% $H_3PO_4$; flow rate=2.5 ml/min, UV detection at 220 nm.

LCMS Method A: ESI, positive ion spectrum; Phenomenex ODS S5 4.6×50 mm column; UV detection at 220 nm; flow rate=4 mL/rain; 4 min continuous gradient from 100% A to 100% B, where A=10% MeOH: 90% $H_2O$:0.1% TFA, and B 90% MeOH: 10% $H_2O$:0.1% TFA LCMS Method B: ESI, positive and negative ion spectra; Phenomenex Luna C18 4.6×50 mm column; UV detection at 220 nm; flow rate=4 mL/min; 4 min continuous gradient from 100% A to 100% B, where A=10:90:MeCN: $H_2O$ (containing 10 mM $NH_4Ac$), and B=90:10 $CH_3CN$: $H_2O$ (containing 10 mM $NH_4Ac$).

Preparative (prep) HPLC was carried out with an automated Shimadzu HPLC system using a continuous of solvent A (10% MeOH/90% $H_2O$/0.2% TFA) vs solvent B (90% MeOH/10% $H_2O$/0.2% TFA). The preparative columns are packed with YMC or Phenomenex ODS C18, 5 micron resin or equivalent.

Abbreviations

The following abbreviations are employed in the Examples and elsewhere herein:
Ph=phenyl
Bn=benzyl
i-Bu=iso-butyl
Me=methyl
Et=ethyl
Pr=propyl
Bu=butyl
AIBN=2,2'-Azobisisobutyronitrile
TMS=trimethylsilyl
$TMSCHN_2$=(trimethylsilyl)diazomethane
FMOC=fluorenylmethoxycarbonyl
Boc or BOC tert-butoxycarbonyl Cbz=carbobenzyloxy or carbobenzoxy or benzyloxycarbonyl
HOAc or AcOH=acetic acid
TBDPSCl=text-butylchlorodiphenylsilane
TMSI=iodotrimethylsilane
DCM=dichloromethane
DEPBT=3-(diethoxyphosphoryloxy)-1,2,3-benzotriazin-4[3H]-one
DIEA=N,N-diisopropylethylamine
DMA=N,N-dimethylacetylamide
DMF=N,N-dimethylformamide
DMSO=dimethylsulfoxide
EtOAc=ethyl acetate
$K_2CO_3$=potassium carbonate
$NaHCO_3$=sodium bicarbonate
THF=tetrahydrofuran
TFA=trifluoroacetic acid
mCPBA=3-Chloroperoxybenzoic acid
NMM=N-methyl morpholine
NBS=N-Bromosuccinimide
DIAD=Diisopropyl azodicarboxylate
DEAD=Diethyl azodicarboxylate
n-BuLi=n-butyllithium
Oxone®=Monopersulfate
Pd/C=palladium on carbon
$PtO_2$=platinum oxide
$H_2O$=water
TEA=triethylamine
EDAC=3-ethyl-3'-(dimethylamino)propyl-carbodiimide hydrochloride (or 1-(3-(dimethyl)amino)propylp-3-ethyl-carbodiimide hydrochloride)
HOBT or HOBT.$H_2O$=1-hydroxybenzotriazole hydrate
HOAT=1-hydroxy-7-azabenzotriazole
PyBOP reagent=benzotriazol-1-yloxy-tripyrrolidino phosphonium hexafluorophosphate
BOP=benzotriazol-1-yloxy-tris(dimethylamino) phosphonium hexafluorophosphate
equiv=equivalent(s)
min=minute(s)
h or hr=hour(s)
L=liter
mL=milliliter
μL=microliter
g=gram(s)
mg=milligram(s)
mol=mole(s)
mmol=millimole(s)
meq=milliequivalent
RT or R.T.=room temperature
sat or sat'd=saturated
aq.=aqueous
TLC=thin layer chromatography
UV=ultraviolet
HPLC=high performance liquid chromatography
HPLC $t_R$=HPLC retention time
LC/MS=high performance liquid chromatography/mass spectrometry
MS or Mass Spec=mass spectrometry
NMR=nuclear magnetic resonance
mp=melting point
$PXPd_2$=Dichloro(chlorodi-tert-butylphosphine)palladium (II) dimer or $[PdCl_2(t-Bu)_2PCl]_2$ The following Examples are illustrative of preferred embodiments of the invention.

Example 1

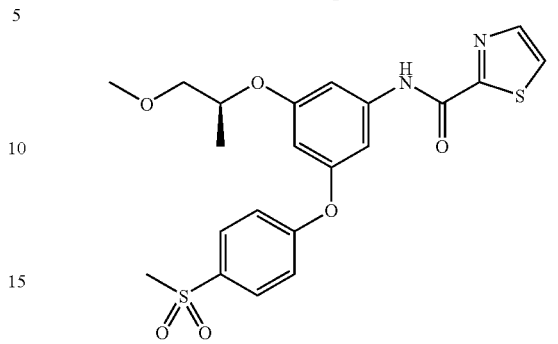

A.

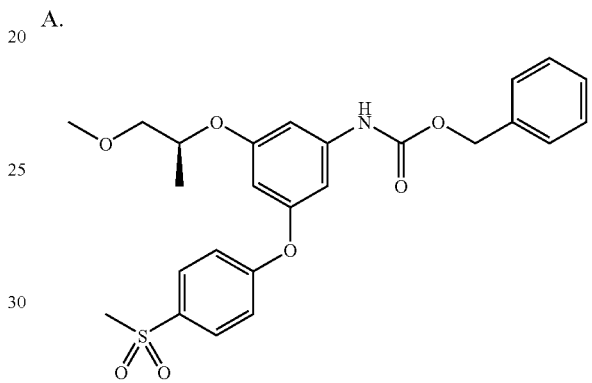

To a RT solution of (S)-3-(1-methoxypropan-2-yloxy)-5-(4-(methylsulfonyl)phenoxy)benzoic acid[1] (2 g, 5.26 mmol) in 1,4-dioxane (25 mL) were successively added PhCH$_2$OH (0.66 mL, 6.31 mmol), Et$_3$N (1.03 mL, 7.36 mmol) and (PhO)$_2$PON$_3$ (1.37 mL, 6.31 mmol). The reaction mixture was stirred at 120° C. overnight. Volatiles were removed in vacuo and the residue was chromatographed ((SiO$_2$; 80 g; continuous gradient from 100% hex to 50:50 hex:EtOAc for 40 min, then hold for 20 min) to give Part A compound (2.12 g, 83% yield) as a white solid. $^1$H NMR (400 MHz, CD$_3$OD) δ ppm 7.90 (d, J=9.2 Hz, 2 H), 7.27-7.40 (m, 5 H), 7.14 (d, J=8.8 Hz, 2 H), 6.96 (s, 1 H), 6.86 (s, 1 H), 6.35 (t, J=2.2 Hz, 1 H), 5.14 (s, 2 H), 4.49-4.56 (m, 1 H), 3.44-3.55 (m, 2 H), 3.36 (s, 3 H), 3.09 (s, 3 H), 1.25 (d, J=6.2 Hz, 3 H); LCMS Method A (ESI, positive ion spectrum): (M+H)/z=486, $t_R$=3.50 min.

B.

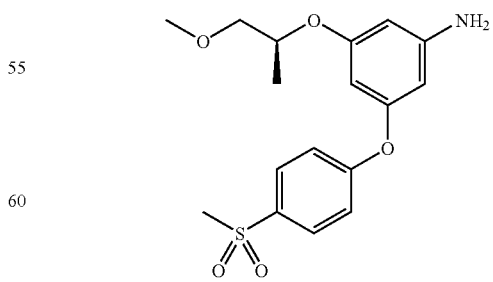

To a solution of Part A Compound (2.11 g, 4.35 mmol) in MeOH (30 mL) was added 10% Pd/C (0.211 g) under Ar at RT with vigorous stirring. The reaction was stirred under 1 atmosphere of H₂ for 1 h, then was filtered through a plug of Celite®. The filtrate was concentrated in vacuo to give Part B Compound (1.52 g, 100%) as a beige sticky oil. LCMS Method A (ESI, positive ion spectrum):(M+H)/z=352, $t_R$=2.17 min.

C.

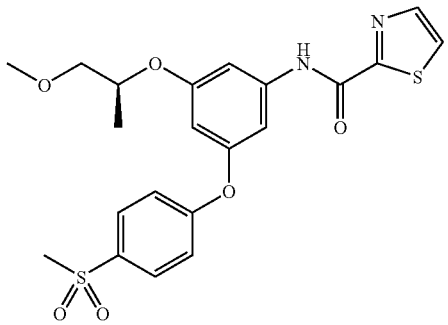

To a RT solution of Part B compound (40 mg, 0.114 mmol) in CH₂Cl₂ (1.5 mL) was added 1,3-thiazole-2-carbonyl chloride (27 mg, 0.185 mmol) followed by Et₃N (59 μL; 0.426 mmol). The reaction mixture was stirred at RT for 2 h, then was diluted with EtOAc (100 mL), washed with H₂O (10 mL) and brine (10 mL), dried (MgSO₄) and concentrated in vacuo.

The crude product was chromatographed (SiO₂; 12 g; continuous gradient from 100% hex to 1:4 hex:EtOAc over 25 min, then held at 1:4 hex:EtOAc for 5 min) to give Part C compound (63 mg, 96% yield) as a white solid. ¹H NMR (500 MHz, CDCl₃) δ ppm 9.09 (s, 1 H), 7.87-7.92 (m, 3 H), 7.64 (d, J=3.3 Hz, 1 H), 7.21 (s, 1 H), 7.13 (d, J=8.8 Hz, 2 H), 7.08 (s, 1 H), 6.47 (s, 1 H), 4.52-4.59 (m, 1 H), 3.54-3.59 (m, 1 H), 3.47-3.52 (m, 1 H), 3.40 (s, 3 H), 3.05 (s, 3 H), 1.32 (d, J=6.0 Hz, 3 H); LCMS Method A (ESI, positive ion spectrum): (M+H)/z=463, $t_R$=3.23 min.

Examples 2 to 5

Examples 2 to 5 were prepared using the same general procedure as described for the synthesis of Example 1 from Example 1 Part B compound and an appropriate acid chloride IIIa

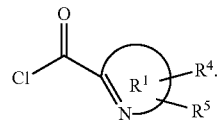

The structures of Examples 1 to 5 and their spectral characterization are shown in Table 1.

TABLE 1

| Example No. | Structure | ¹H NMR, (M + H)/z, LCMS $t_R$ |
|---|---|---|
| 1 | 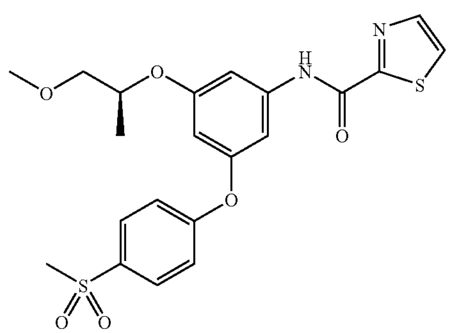 | ¹H NMR (500 MHz, CDCl₃) δ ppm 9.09 (s, 1 H), 7.87-7.92 (m, 3 H), 7.64 (d, J = 3.3 Hz, 1 H), 7.21 (s, 1 H), 7.13 (d, J = 8.8 Hz, 2 H), 7.08 (s, 1 H), 6.47 (s, 1 H), 4.52-4.59 (m, 1 H), 3.54-3.59 (m, 1 H), 3.47-3.52 (m, 1 H), 3.40 (s, 3 H), 3.05 (s, 3 H), 1.32 (d, J = 6.0 Hz, 3 H); LCMS Method A (ESI, positive ion spectrum): (M + H)/z = 463, $t_R$ = 3.23 min. |
| 2 | 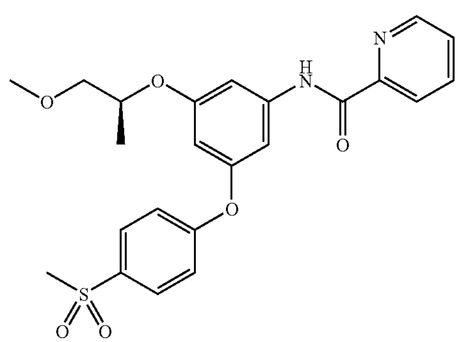 | ¹H NMR (400 MHz, CDCl₃) δ ppm 10.13 (s, 1 H), 8.61 (d, J = 4.0 Hz, 1 H), 8.28 (d, J = 7.9 Hz, 1 H), 7.91-7.97 (m, 1 H), 7.88 (d, J = 9.2 Hz, 2 H), 7.52 (dd, J = 6.6, 4.8 Hz, 1 H), 7.30-7.33 (m, 1 H), 7.16-7.20 (m, 1 H), 7.13 (d, J = 8.8 Hz, 2 H), 6.46 (t, J = 2.2 Hz, 1 H), 4.53-4.62 (m, 1 H), 3.55-3.61 (m, 1 H), 3.47-3.52 (m, 1 H), 3.41 (s, 3 H), 3.05 (s, 3 H), 1.33 (d, J = 6.2 Hz, 3 H); LCMS Method A (ESI, positive ion spectrum): (M + H)/z = 457, $t_R$ = 3.28 min. |

TABLE 1-continued

| Example No. | Structure | ¹H NMR, (M + H)/z, LCMS $t_R$ |
|---|---|---|
| 3 | 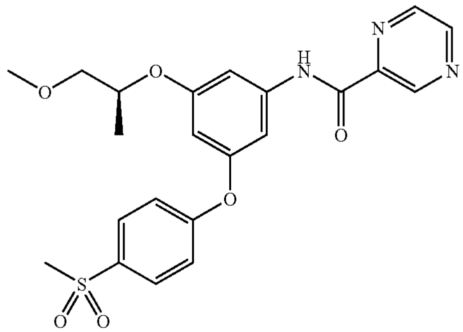 | ¹H NMR (500 MHz, CDCl₃) δ ppm 9.66 (s, 1 H), 9.48 (s, 1 H), 8.82 (d, J = 2.2 Hz, 1 H), 8.58 (s, 1 H), 7.89 (d, J = 8.8 Hz, 2 H), 7.29 (s, 1 H), 7.11-7.16 (m, J = 8.8 Hz, 3 H), 6.48 (s, 1 H), 4.54-4.61 (m, 1 H), 3.58 (dd, J = 10.4, 6.0 Hz, 1 H), 3.48-3.52 (m, 1 H), 3.41 (s, 3 H), 3.06 (s, 3 H), 1.33 (d, J = 6.6 Hz, 3 H); LCMS Method A (ESI, positive ion spectrum): (M + H)/z = 458, $t_R$ = 3.08 min. |
| 4 | 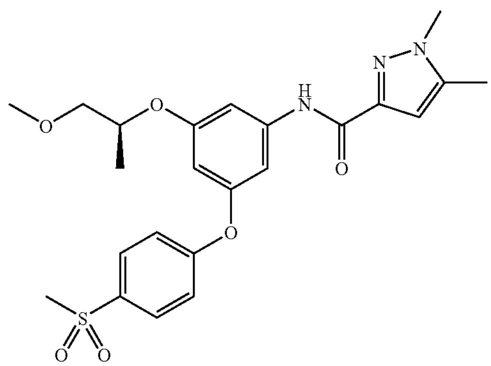 | ¹H NMR (500 MHz, CDCl₃) δ ppm 8.65 (s, 1 H), 7.87 (d, J = 8.8 Hz, 2 H), 7.22 (s, 1 H), 7.12 (d, J = 8.8 Hz, 2 H), 7.04 (s, 1 H), 6.59 (s, 1 H), 6.41 (s, 1 H), 4.51-4.59 (m, 1 H), 3.81 (s, 3 H), 3.53-3.60 (m, 1 H), 3.46-3.51 (m, 1 H), 3.40 (s, 3 H), 3.05 (s, 3 H), 2.30 (s, 3 H), 1.32 (d, J = 6.0 Hz, 3 H); LCMS Method B (ESI, pos./neg. ion spectrum): (M + H)/z = 474, $t_R$ = 3.04 min. |
| 5 | 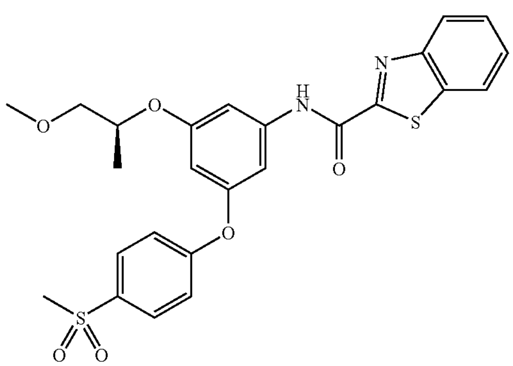 | ¹H NMR (500 MHz, CDCl₃) δ ppm 9.25 (s, 1 H), 8.11 (d, J = 8.2 Hz, 1 H), 8.00 (d, J = 8.2 Hz, 1 H), 7.90 (d, J = 8.8 Hz, 2 H), 7.59 (t, J = 7.1 Hz, 1 H), 7.53 (t, J = 7.4 Hz, 1 H), 7.29 (s, 1 H), 7.11-7.17 (m, 3 H), 6.50 (s, 1 H), 4.54-4.62 (m, 1 H), 3.56-3.61 (m, 1 H), 3.49-3.53 (m, 1 H), 3.41 (s, 3 H), 3.06 (s, 3 H), 1.34 (d, J = 6.6 Hz, 3 H); LCMS Method A (ESI, positive ion spectrum): (M + H)/z = 513, $t_R$ = 3.69 min. |

Example 6

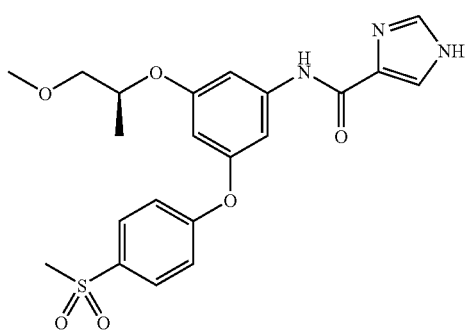

A.

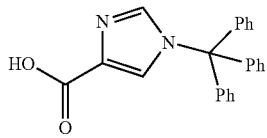

To a RT solution of 1H-imidazole-4-carboxylic acid (1.12 g, 9.99 mmol) in pyridine (15 mL) and DMF (30 mL) was added triphenylmethyl chloride (3.06 g, 11.0 mmol). The reaction mixture was stirred at RT overnight, then was partitioned between EtOAc (500 mL) and H₂O (50 mL). The organic phase was washed with H₂O (20 mL), 10% citric acid (20 mL) and brine (5 mL), dried (MgSO₄) and concentrated in vacuo. The residue was triturated with EtOAc to afford 1-trityl-1H-imidazole-4-carboxylic acid (2.78 g, 79% yield) as a white solid. LCMS Method A (ESI, positive ion spectrum): (M+H)/z=not observed, $t_R$=3.27 min.

B.

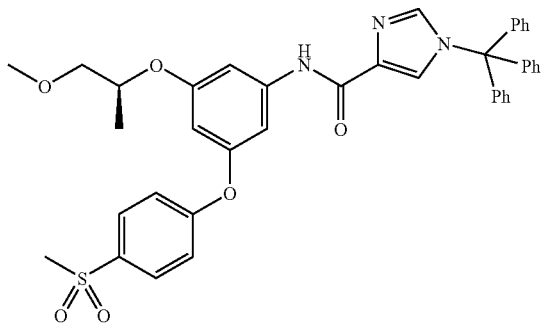

BOP (503 mg, 1.14 mmol) was added to a RT solution of Part A compound (403 mg, 1.14 mmol) in CH$_2$Cl$_2$ (5 mL), followed by Et$_3$N (0.32 mL; 2.28 mmol). After stirring at RT for 10 min, Example 1 Part A compound (200 mg, 0.569 mmol) was added. The reaction was stirred at RT for 72 h; LCMS indicated complete consumption of Example 1 Part A compound. The crude Part B compound was directly used in the next step without further purification. LCMS Method A (ESI, positive ion spectrum): (M+H)/z=not observed, t$_R$=3.47 min.

C.

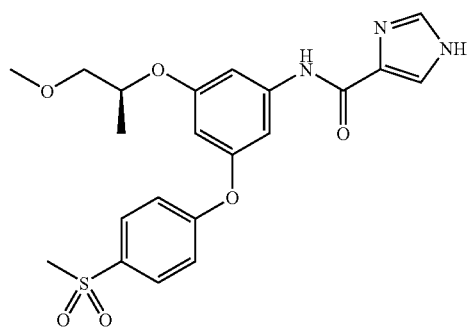

TFA (5 mL) was added to the crude Part B compound and the mixture was stirred at RT for 10 min. Volatiles were removed in vacuo and the residue was chromatographed (SiO$_2$; 40 g; continuous gradient from 100:0 hex:EtOAc to 0:100 hex:EtOAc over 30 min, then held at 100% EtOAc for 20 min) to give the title compound (215 mg, 85% yield) as a white solid. $^1$H NMR (500 MHz, CDCl$_3$) δ ppm 7.93 (d, J=8.8 Hz, 2 H), 7.77 (s, 2 H), 7.25 (s, 1 H), 7.20 (d, J=8.8 Hz, 2 H), 7.16 (s, 1 H), 6.45-6.47 (m, 1 H), 4.56-4.61 (m, 1 H), 3.54-3.58 (m, 1 H), 3.49-3.53 (m, 1 H), 3.38 (s, 3 H), 3.11 (s, 3 H), 1.29 (d, J=6.0 Hz, 3 H); LCMS Method. A (ESI, positive ion spectrum): (M+H)/z 446, t$_R$=2.57 min.

Examples 7 to 20

Examples 7 to 20 were prepared using the same general procedure as described for the synthesis of Example 6 Part B Compound from Example 6 Part A Compound and an appropriate carboxylic acid IIb (Scheme 1)

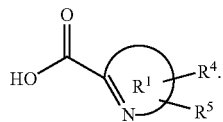

IIb

The structures of Examples 7 to 20 and their spectral characterization are shown in Table 2.

TABLE 2

| Example No | Structure | $^1$H NMR, (M + H)/z, LCMS t$_R$ |
|---|---|---|
| 7 | 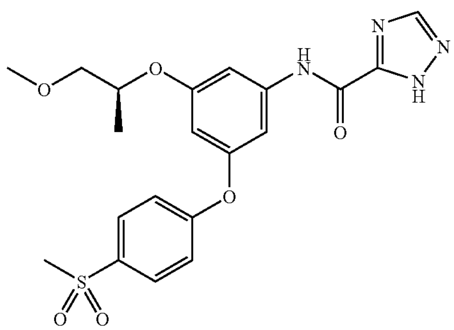 | $^1$H NMR (500 MHz, CDCl$_3$/CD$_3$OD) δ ppm 8.14 (s, 1 H), 7.86 (d, J = 8.8 Hz, 2 H), 7.17 (s, 1 H), 7.08-7.13 (m, 3 H), 6.44 (s, 1 H), 4.52 (dd, J = 10.4, 6.0 Hz, 1 H), 3.52-3.58 (m, 1 H), 3.44-3.49 (m, 1 H), 3.38 (s, 3 H), 3.03 (s, 3 H), 1.29 (d, J = 6.6 Hz, 3 H); LCMS Method A (ESI, positive ion spectrum): (M + H)/z = 447, t$_R$ =2.80 min. |

TABLE 2-continued

| Example No | Structure | ¹H NMR, (M + H)/z, LCMS $t_R$ |
|---|---|---|
| 8 | 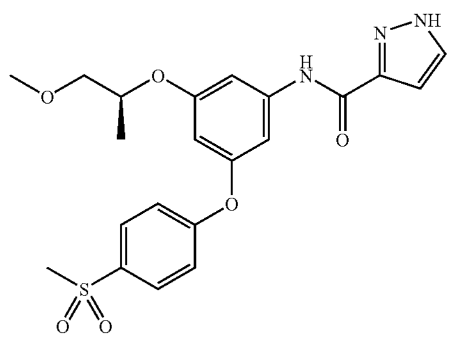 | ¹H NMR (500 MHz, CDCl₃) δ ppm 8.77 (s, 1 H), 7.87 (d, J = 8.8 Hz, 2 H), 7.62 (d, J = 2.2 Hz, 1 H), 7.21 (s, 1 H), 7.12 (d, J = 8.8 Hz, 2 H), 7.04 (s, 1 H), 6.92 (d, J = 2.2 Hz, 1 H), 6.42 (s, 1 H), 4.51-4.60 (m, 1 H), 3.55-3.61 (m, 1 H), 3.47-3.53 (m, 1 H), 3.41 (s, 3 H), 3.05 (s, 3 H), 1.31 (d, J = 6.6 Hz, 3 H); LCMS Method A (ESI, positive ion spectrum): (M + H)/z = 446, $t_R$ = 2.97 min. |
| 9 | 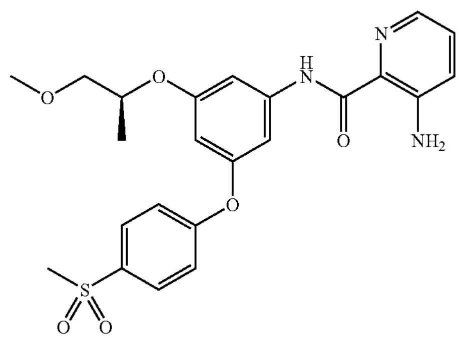 | ¹H NMR (500 MHz, CDCl₃) δ ppm 10.13 (s, 1 H), 7.85-7.91 (m, 3 H), 7.18-7.23 (m, 2 H), 7.11-7.15 (m, 3 H), 7.03 (d, J = 8.2 Hz, 1 H), 6.42 (s, 1 H), 5.97 (s, 2 H), 4.52-4.60 (m, 1 H), 3.58 (dd, J = 10.2, 5.8 Hz, 1 H), 3.46-3.52 (m, 1 H), 3.40 (s, 3 H), 3.05 (s, 3 H), 1.32 (d, J = 6.0 Hz, 3 H); LCMS Method A (ESI, positive ion spectrum): (M + H)/z = 472, $t_R$ = 3.35 min. |
| 10 | 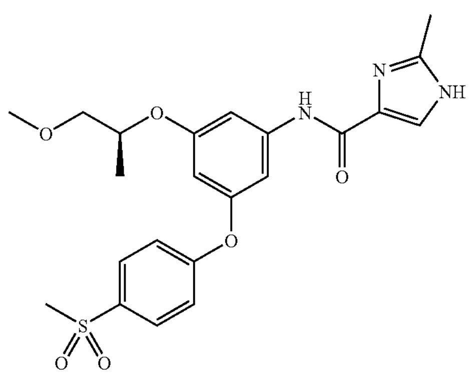 | ¹H NMR (400 MHz, CD₃OD) δ ppm 7.95 (s, 1 H), 7.81 (d, J = 8.8 Hz, 2 H), 7.28 (s, 1 H), 7.13 (d, J = 1.8 Hz, 2 H), 7.07 (d, J = 8.8 Hz, 2 H), 6.38-6.41 (m, 1 H), 4.44-4.54 (m, 1 H), 3.49-3.55 (m, 1 H), 3.42-3.48 (m, 1 H), 3.35 (s, 3 H), 3.01 (s, 3 H), 2.60 (s, 3 H), 1.25 (d, J = 6.2 Hz, 3 H); LCMS Method A (ESI, positive ion spectrum): (M + H)/z = 460, $t_R$ = 2.55 min. |
| 11 | 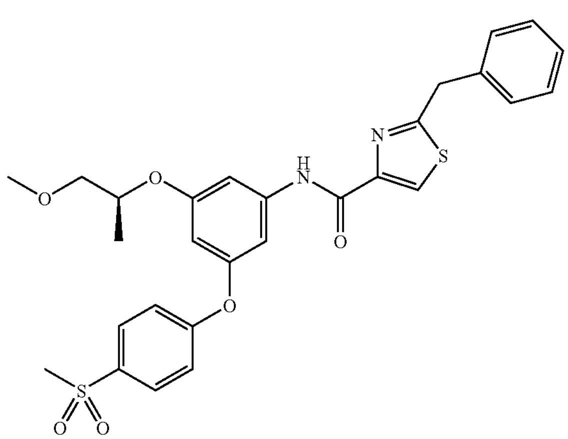 | ¹H NMR (400 MHz, CDCl₃) δ ppm 9.20 (s, 1 H), 8.04 (s, 1 H), 7.88 (d, J = 8.8 Hz, 2 H), 7.27-7.40 (m, 5 H), 7.13 (d, J = 8.8 Hz, 2 H), 7.09 (s, 1 H), 6.45 (t, J = 2.2 Hz, 1 H), 4.51-4.62 (m, 1 H), 4.33 (s, 2 H), 3.54-3.61 (m, 1 H), 3.46-3.52 (m, 1 H), 3.41 (s, 3 H), 3.05 (s, 3 H), 1.33 (d, J = 6.2 Hz, 3 H); LCMS Method A (ESI, positive ion spectrum): (M + H)/z = 553, $t_R$ = 3.70 min. |

TABLE 2-continued

| Example No | Structure | ¹H NMR, (M + H)/z, LCMS $t_R$ |
|---|---|---|
| 12 | 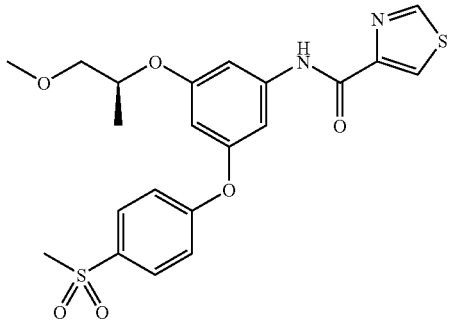 | ¹H NMR (400 MHz, CDCl₃) δ ppm 9.27 (s, 1 H), 8.80 (d, J = 2.2 Hz, 1 H), 8.27 (d, J = 2.2 Hz, 1 H), 7.88 (d, J = 8.8 Hz, 2 H), 7.22 (s, 1 H), 7.13 (d, J = 8.8 Hz, 2 H), 7.09 (s, 1 H), 6.45 (s, 1 H), 4.52-4.61 (m, 1 H), 3.55-3.61 (m, 1 H), 3.48-3.53 (m, 1 H), 3.41 (s, 3 H), 3.05 (s, 3 H), 1.32 (d, J = 6.6 Hz, 3 H); LCMS Method A (ESI, positive ion spectrum): (M + H)/z = 463, $t_R$ = 3.10 min. |
| 13 | 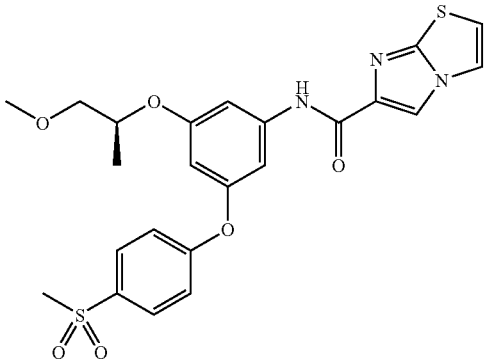 | ¹H NMR (500 MHz, CDCl₃) δ ppm 9.00 (s, 1 H), 8.09 (s, 1 H), 7.88 (d, J = 8.8 Hz, 2 H), 7.50 (d, J = 4.4 Hz, 1 H), 7.22 (s, 1 H), 7.09-7.16 (m, 3 H), 6.98 (d, J = 4.9 Hz, 1 H), 6.41-6.45 (m, 1 H), 4.51-4.60 (m, 1 H), 3.55-3.60 (m, 1 H), 3.47-3.52 (m, 1 H), 3.40 (s, 3 H), 3.05 (s, 3 H), 1.32 (d, J = 6.0 Hz, 3 H); LCMS Method A (ESI, positive ion spectrum): (M + H)/z = 502, $t_R$ = 3.18 min. |
| 14 | 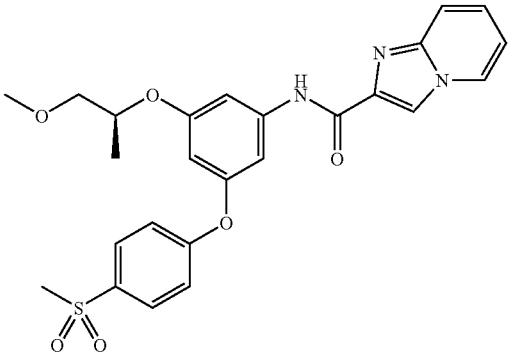 | ¹H NMR (500 MHz, CDCl₃) δ ppm 9.24 (s, 1 H), 8.14-8.20 (m, 2 H), 7.89 (d, J = 8.8 Hz, 2 H), 7.59 (d, J = 8.8 Hz, 1 H), 7.26-7.32 (m, 2 H), 7.11-7.17 (m, 3 H), 6.89 (t, J = 6.3 Hz, 1 H), 6.42-6.47 (m, 1 H), 4.52-4.61 (m, 1 H), 3.55-3.61 (m, 1 H), 3.47-3.53 (m, 1 H), 3.41 (s, 3 H), 3.06 (s, 3 H), 1.33 (d, J = 6.0 Hz, 3 H); LCMS Method A (ESI, positive ion spectrum): (M + H)/z = 496, $t_R$ = 2.76 min. |
| 15 | 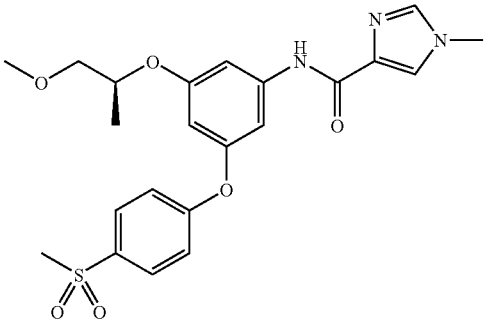 | ¹H NMR (500 MHz, CDCl₃) δ ppm 9.90 (s, 1 H), 8.47 (s, 1 H), 7.84-7.91 (m, 3 H), 7.08-7.16 (m, 4 H), 6.47 (s, 1 H), 4.52-4.60 (m, 1 H), 3.97 (s, 3 H), 3.58-3.64 (m, 1 H), 3.52-3.57 (m, 1 H), 3.43 (s, 3 H), 3.05 (s, 3 H), 1.30 (d, J = 6.0 Hz, 3 H); LCMS Method A (ESI, positive ion spectrum): (M + H)/z = 460, $t_R$ = 2.57 min. |

TABLE 2-continued

| Example No | Structure | ¹H NMR, (M + H)/z, LCMS $t_R$ |
| --- | --- | --- |
| 16 | 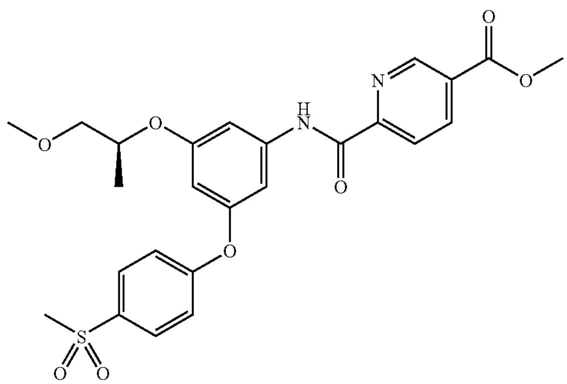 | ¹H NMR (500 MHz, CDCl₃) δ ppm 10.01 (s, 1 H), 9.18 (s, 1 H), 8.48-8.53 (m, 1 H), 8.33 (d, J = 8.2 Hz, 1 H), 7.89 (d, J = 8.8 Hz, 2 H), 7.30 (s, 1 H), 7.17 (s, 1 H), 7.14 (d, J = 9.3 Hz, 2 H), 6.47 (s, 1 H), 4.54-4.62 (m, 1 H), 3.99 (s, 3 H), 3.58 (dd, J = 9.9, 6.0 Hz, 1 H), 3.49-3.52 (m, 1 H), 3.41 (s, 3 H), 3.05 (s, 3 H), 1.33 (d, J = 6.6 Hz, 3 H); LCMS Method A (ESI, positive ion spectrum): (M + H)/z = 515, $t_R$ = 3.47 min. |
| 17 | 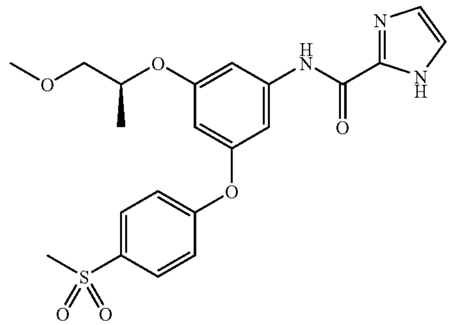 | ¹H NMR (400 MHz, CDCl₃) δ ppm 11.09 (s, 1 H), 7.88 (d, J = 7.0 Hz, 2 H), 7.41 (s, 2 H), 7.04-7.14 (m, 4 H), 6.45 (d, J = 1.8 Hz, 1 H), 4.50-4.65 (m, 1 H), 3.55-3.70 (m, 2 H), 3.46 (s, 3 H), 3.06 (s, 3 H), 1.31 (d, J = 4.8 Hz, 3 H); LCMS Method A (ESI, positive ion spectrum): (M + H)/z = 446, $t_R$ = 2.74 min. |
| 18 | 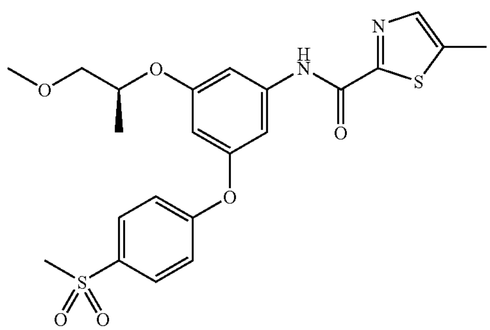 | ¹H NMR (500 MHz, CDCl₃) δ ppm 8.99 (s, 1 H), 7.88 (d, J = 8.8 Hz, 2 H), 7.55 (s, 1 H), 7.19 (s, 1 H), 7.12 (d, J = 8.8 Hz, 2 H), 7.06 (s, 1 H), 6.43-6.47 (m, 1 H), 4.50-4.60 (m, 1 H), 3.55-3.59 (m, 1 H), 3.46-3.51 (m, 1 H), 3.40 (s, 3 H), 3.05 (s, 3 H), 2.56 (s, 3 H), 1.32 (d, J = 6.0 Hz, 3 H); LCMS Method A (ESI, positive ion spectrum): (M + H)/z = 477, $t_R$ = 3.03 min. |
| 19 | 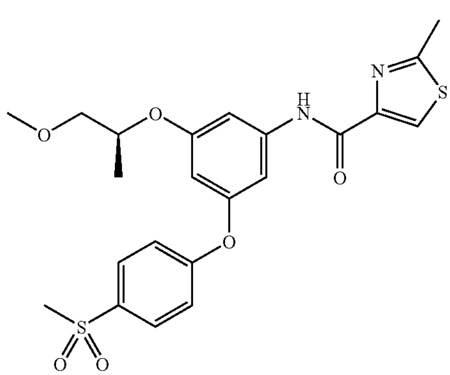 | ¹H NMR (500 MHz, CDCl₃) δ ppm 9.19 (s, 1 H), 8.02 (s, 1 H), 7.88 (d, J = 8.8 Hz, 2 H), 7.25 (s, 1 H), 7.13 (d, J = 8.8 Hz, 2 H), 7.07 (s, 1 H), 6.43-6.45 (m, 1 H), 4.51-4.60 (m, 1 H), 3.54-3.60 (m, 1 H), 3.47-3.51 (m, 1 H), 3.40 (s, 3 H), 3.05 (s, 3 H), 2.74 (s, 3 H), 1.32 (d, J = 6.6 Hz, 3 H); LCMS Method A (ESI, positive ion spectrum): (M + H)/z = 477, $t_R$ = 3.29 min. |

TABLE 2-continued

| Example No | Structure | $^1$H NMR, (M + H)/z, LCMS $t_R$ |
|---|---|---|
| 20 | 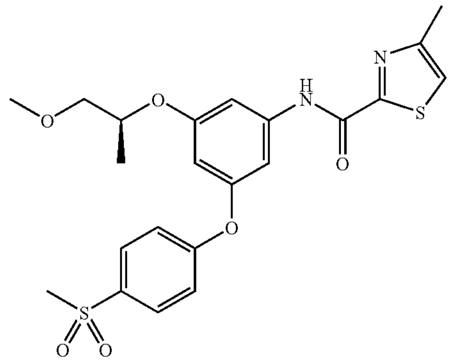 | $^1$H NMR (500 MHz, CD$_3$OD) δ ppm 7.93 (d, J = 8.8 Hz, 2 H), 7.46 (s, 1 H), 7.31 (s, 1 H), 7.18-7.22 (m, 3 H), 6.49-6.52 (m, 1 H), 4.56-4.63 (m, 1 H), 3.54-3.58 (m, 1 H), 3.49-3.53 (m, 1 H), 3.38 (s, 3 H), 3.11 (s, 3 H), 2.51 (s, 3 H), 1.29 (d, J = 6.0 Hz, 3 H); LCMS Method A (ESI, positive ion spectrum): (M + H)/z = 477, $t_R$ = 3.39 min. |

Example 21

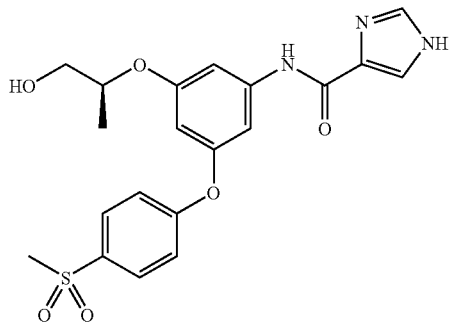

TMSI (92 μL, 0.675 mmol) was added to a solution of Example 6 compound (60 mg, 0.135 mmol) in dry MeCN (0.6 mL) at RT under Ar. The reaction mixture was stirred at RT overnight, then was quenched with. H$_2$O (5 mL) and volatiles were removed in vacuo. The residue was diluted with EtOAc (10 mL) and 1N aqueous HCl (5 mL). After stirring for 5 min, the aqueous layer was neutralized to pH ~7-8 with solid K$_2$CO$_3$. The aqueous layer was extracted with EtOAc (2×20 mL). The combined organic extracts were washed with 10% (w/v) aqueous Na$_2$S$_2$O$_3$.5H$_2$O (10 mL) to remove residual iodine, washed with brine (10 mL), dried (MgSO$_4$) and concentrated in vacuo. The crude product was purified by preparative HPLC (YMC reverse phase ODS-A-5 μm 30×100 mm column; flow rate=40 mL/min, continuous gradient from 4:1 A:B to 100% solvent B over 12 min, then held for another 4 min at 100% B, where solvent A=90:10 H$_2$O:MeOH and solvent B=90:10 MeOH:H$_2$O) to give the title compound (31 mg, 53% yield) as a white solid. $^1$H NMR (500 MHz, CDCl$_3$/CD$_3$OD) δ ppm 7.78 (d, J=8.8 Hz, 2 H), 7.61 (s, 1 H), 7.51 (s, 1 H), 7.13 (s, 1 H), 7.05 (d, J=8.8 Hz, 2 H), 7.01 (d, J=2.2 Hz, 1 H), 6.33 (d, J=2.2 Hz, 1 H), 4.32-4.41 (m, 1 H), 3.59-3.65 (m, 1 H), 3.54-3.59 (m, 1 H), 3.25 (s, 3 H), 1.21 (d, J=6.6 Hz, 3 H); LCMS Method A (ESI, positive ion spectrum): (M+H)/z=432, $t_R$=2.46 min.

Example 22

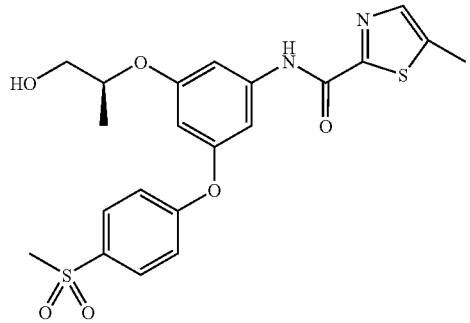

The title compound (27.5 mg; 94% yield; white solid) was prepared from Example 18 (30 mg; 0.063 mmol) using an analogous procedure to that described for the synthesis of Example 21. $^1$H NMR (500 MHz, CD$_3$OD) δ ppm 7.93 (d, J=8.8 Hz, 2 H), 7.67 (s, 1 H), 7.30 (s, 1 H), 7.17-7.22 (m, 3 H), 6.51 (s, 1 H), 4.43-4.52 (m, 1 H), 3.61-3.70 (m, 2 H), 3.11 (s, 3 H), 2.56 (s, 3 H), 1.29 (d, J=6.0 Hz, 3 H); LCMS Method A (ESI, positive ion spectrum): (M+H)/z=463, $t_R$=3.09 min.

Example 23

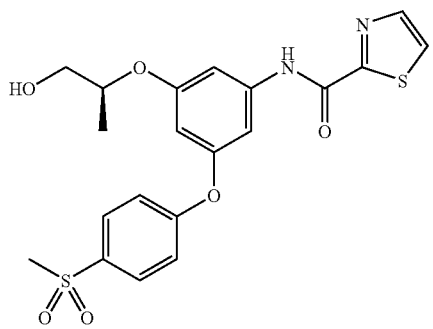

1,3-Thiazole-2-carbonyl chloride (26 mg, 0.178 mmol) was added to a mixture of Compound 24D (30 mg, 0.089 mmol) in THF (1 mL) and saturate aqueous solution of NaHCO$_3$ (1 mL) at RT. The reaction mixture was vigorously stirred at RT for o/n. The reaction was diluted with EtOAc (5 mL). The layers were separated. The aqueous layer was extracted with EtOAc (2×10 mL). The combined organic extracts were washed with brine (5 mL), dried (MgSO$_4$), and concentrated in vacuo. The crude residue was chromatographed (SiO$_2$; 12 g; continuous gradient from 100:0 hexanes:EtOAc to 0:70% hexanes:EtOAc over 25 min, held at 70% EtOAc for 15 min) to give the title compound (24.8 mg, 62% yield) as a white solid. $^1$H NMR (500 MHz, CDCl$_3$) δ ppm 9.11 (s, 1 H), 7.88-7.94 (m, 3 H), 7.65 (d, J=3.3 Hz, 1 H), 7.27 (s, 1 H), 7.14 (d, J=8.8 Hz, 2 H), 7.05 (s, 1 H), 6.45-6.48 (m, 1 H), 4.48-4.56 (m, 1 H), 3.69-3.79 (m, 2 H), 3.06 (s, 3 H), 1.31 (d, J=6.6 Hz, 3 H); LCMS Method A (ESI, positive ion spectrum): (M+H)/z=449, $t_R$=2.93 min.

Example 24

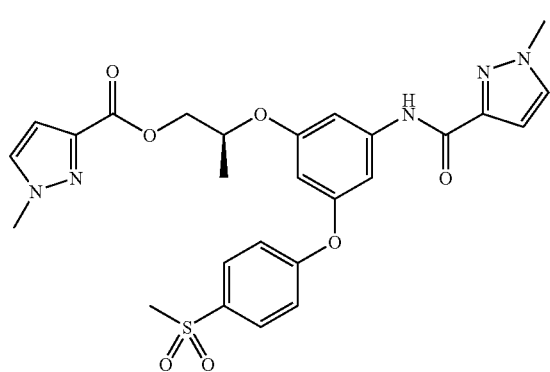

A.

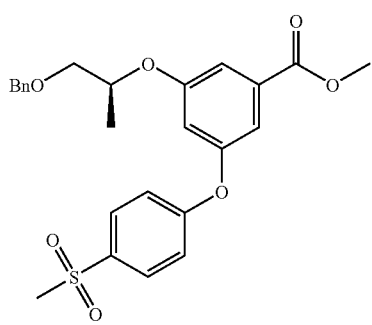

A solution of 3-hydroxy-5-(4-(methylsulfonyl)phenoxy)benzoate[2] (3.7 g, 11.5 mmol), (R)-(-)-1-Benzyloxy-2-propanol (2.5 g, 15 mmol), polymer-supported Ph$_3$P (30 g of 1 mmol/g, 30 mmol) in 150 mL of THF was added dropwise a solution of DIAD (3.4 mL, 17.3 mmol) over 15 min under N$_2$ (internal temperature maintained at ≦5° C.). The reaction mixture was allowed to warm to RT overnight, then filtered. The solids were thoroughly washed with THF and CH$_2$Cl$_2$. The combined filtrates were concentrated in vacuo. The mixture was chromatographed on silica gel column (EtOAc/Hexane; 1:1) to give 6 g of slightly impure Part A compound (6 g, 110%) as a colorless oil. [M+H]=471; $^1$H NMR (400 MHz, chloroform-d) δ ppm 7.90 (2 H, d, J=8.79 Hz), 7.48 (1 H, s), 7.27-7.37 (6 H, m), 7.09 (2 H, d, J=8.79 Hz), 6.83-6.89 (1 H, m), 4.60-4.69 (1 H, m), 4.58 (2 H, s), 3.90 (3 H, s), 3.54-3.70 (2 H, m), 3.06 (3 H, s), 1.34 (3 H, d, J=6.15 Hz).

B.

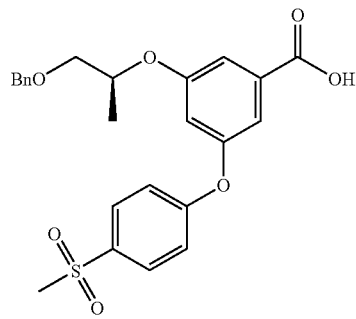

A solution of Part A (6 g, 13 mmol), LiOH (1.6 g, 39 mmol) and H$_2$O (50 mL) in THF (20 mL) was stirred at RT for 3 h and then was concentrated in vacuo. The water solution was washed with ether (15 ml×4), neutralized to pH=4 with concentrated HCl, extracted with EtOAc (50 mL). The organic layer was washed with H$_2$O, and dried (MgSO$_4$), filtered, and concentrated in vacuo to give Part B compound (5 g, 95%) as an white solid. [M+H]=457; $^1$H NMR (400 MHz, chloroform-d) δ ppm 7.91 (2 H, d, J=8.79 Hz), 7.52 (1 H, s), 7.27-7.38 (6 H, m), 7.11 (2 H, d, J=8.79 Hz), 6.90 (1 H, t, J=2.20 Hz), 4.61-4.70 (1 H, m), 4.59 (2 H, s), 3.56-3.70 (2 H, m), 3.07 (3 H, s), 1.35 (3 H, d, J=6.59 Hz).

C.

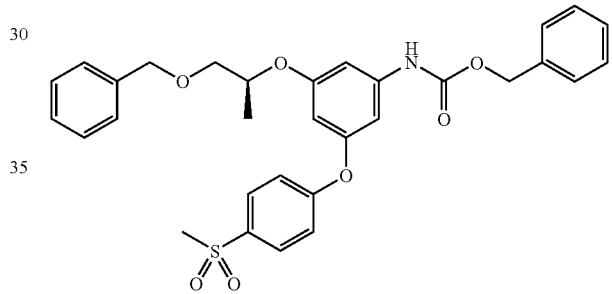

To a RT solution of Part B Compound (630 mg, 1.38 mmol) in 1,4-dioxane (6 mL) were successively added PhCH$_2$OH (0.17 mL, 1.66 mop, Et$_3$N (0.27 mL, 1.93 mmol) and (PhO)$_2$PON$_3$ (0.36 mL, 1.66 mmol). The reaction mixture was stirred at 120° C. overnight, then was cooled to RT. Volatiles were removed in vacuo and the residue was chromatographed (SiO$_2$; 120 g; continuous gradient from 100% hexanes to 1:1 hex:EtOAc over 40 min, then held at 1:1 hex:EtOAc for 20 min) to give Part C compound (571 mg, 74% yield) as a white solid. LCMS Method A (ESI, positive ion spectrum): (M+H)/z=562, $t_R$=3.96 min.

D.

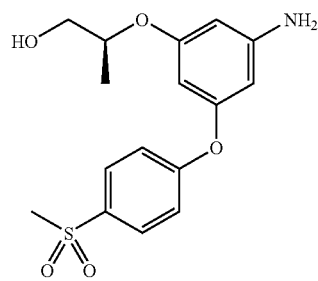

To a solution of Part C compound (570 mg, 1.02 mmol) in MeOH (30 mL) was added 10% Pd/C (57 mg, 0.536 mmol)

under Ar at RT with vigorous stirring. The reaction was stirred under 1 atm of $H_2$ for 6 h, then was filtered through Celite®. The filtrate was concentrated in vacuo to give Part D Compound (312 mg, 91% yield) as a white solid. LCMS Method A (ESI, positive ion spectrum): (M+H)/z=338, $t_R$=1.89 min.

E.

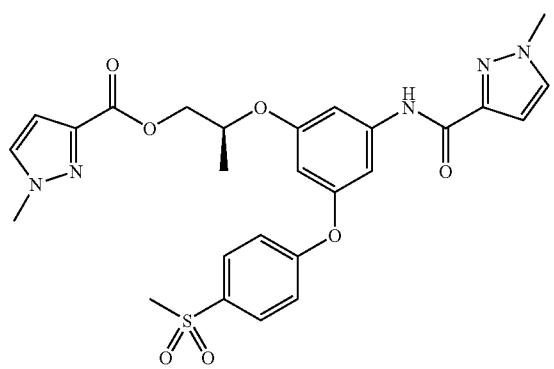

BOP (104 mg, 0.236 mmol) was added to a solution of 1-methyl-1H-pyrazole-3-carboxylic acid (30 mg, 0.236 mmol) in $CH_2Cl_2$ (0.6 mL) at RT, followed by $Et_3N$ (0.050 mL; 0.354 mmol). After stirring at RT for 10 min, Part D compound (20 mg, 0.059 mmol) was added. The reaction was stirred at RT for 48 h, then was directly chromatographed ($SiO_2$; 12 g; continuous gradient from 20:80 hex:EtOAc to 100% EtOAc over 10 min, held at 100% EtOAc for 20 min) to give Part E compound (32.2 mg, 92% yield) as a white solid. $^1$H NMR (500 MHz, $CDCl_3$) δ ppm 8.70 (s, 1 H), 7.86 (d, J=8.8 Hz, 2 H), 7.40 (d, J=2.2 Hz, 1 H), 7.35 (d, J=2.2 Hz, 1 H), 7.17 (s, 1 H), 7.07-7.13 (m, 3 H), 6.84 (d, J=2.2 Hz, 1 H), 6.74 (d, J=2.2 Hz, 1 H), 6.45 (s, 1 H), 4.72-4.81 (m, 1 H), 4.53 (dd, J=11.5, 6.6 Hz, 1 H), 4.39 (dd, J=11.5, 3.8 Hz, 1 H), 3.95 (d, J=2.7 Hz, 6 H), 3.05 (s, 3 H), 1.41 (d, J=6.6 Hz, 3 H); LCMS Method A (ESI, positive ion spectrum): (M+H)/z=554, $t_R$=3.03 min.

Example 25

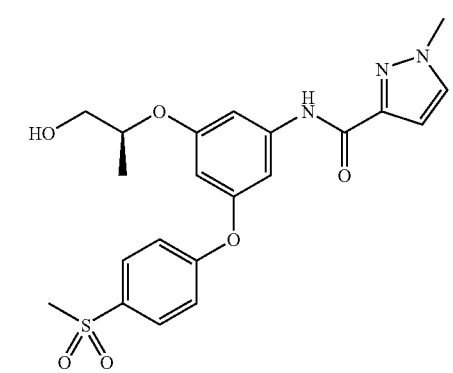

KOH (8 mg, 0.135 mmol) was added to a solution of Example 24 (30 mg, 0.054 mmol) in MeOH (1 mL)/THF (1 mL)/$H_2O$ (0.5 mL). The reaction was stirred at RT for 1 h; volatiles were removed in vacuo and the residue was partitioned between EtOAc (50 mL) and $H_2O$ (5 mL). The aqueous layer was extracted with EtOAc (2×10 mL). The combined organic extracts were washed with brine (5 mL), dried ($MgSO_4$), and concentrated in vacuo. The crude residue was chromatographed ($SiO_2$; 12 g; continuous gradient from 100:0 hex:EtOAc to 0:100% Hex:EtOAc over 10 min, held at 100% EtOAc for 20 min) to give the title compound (7 mg, 32% yield) as a colorless sticky oil. $^1$H NMR (500 MHz, $CDCl_3$) δ ppm 8.68 (s, 1 H), 7.89 (d, J=8.8 Hz, 2 H), 7.40 (d, J=2.2 Hz, 1 H), 7.30 (s, 1 H), 7.13 (d, J=8.8 Hz, 2 H), 7.00 (s, 1 H), 6.84 (d, J=2.2 Hz, 1 H), 6.41 (s, 1 H), 4.47-4.56 (m, 1 H), 3.95 (s, 3 H), 3.68-3.78 (m, 2 H), 3.05 (s, 3 H), 1.30 (d, J=6.6 Hz, 3 H); LCMS Method A (ESI, positive ion spectrum): (M+H)/z=446, $t_R$=2.72 min.

Example 26

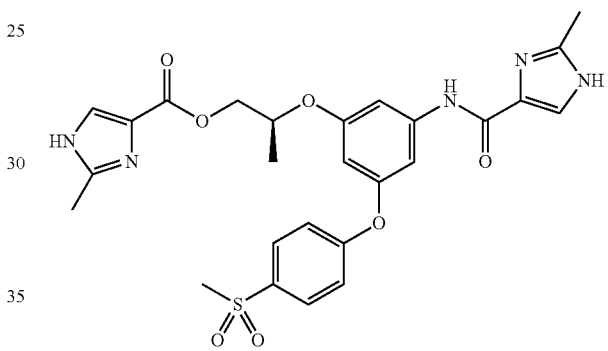

BOP (262 mg, 0.592 mmol) was added to a solution of 2-methyl-1H imidazole-4-carboxylic acid monohydrate (85 mg, 0.592 mmol) in pyridine (1.5 mL) at RT, followed by $Et_3N$ (0.12 mL; 0.888 mmol). After stirring at RT for 10 min, Example 24 Part D compound (50 mg, 0.148 mmol) was added. The reaction was heated at 80° C. overnight, then was cooled to RT. Volatiles were removed in vacuo and the residue was partitioned between EtOAc (100 mL) and $H_2O$ (10 mL). The aqueous layer was extracted with EtOAc (2×10 mL). The combined organic extracts were washed with brine (5 mL), dried ($MgSO_4$), and concentrated in vacuo. The crude residue was purified by preparative HPLC (YMC reverse phase ODS-A-5 μm 30×100 mm column; flow rate=40 mL/min, continuous gradient from 4:1 A:B to 100% solvent B over 10 min, then held at 100% B for 2 min, where solvent A=90:10:0.1$H_2O$:MeOH:TFA and solvent B=90:10:0.1 MeOH:$H_2O$:TFA) to give the title compound (27.5 mg, 34% yield) as a white solid. $^1$H NMR (500 MHz, $CD_3OD$) δ ppm 7.91 (d, J=8.8 Hz, 2 H), 7.63 (s, 1 H), 7.53 (s, 1 H), 7.26 (s, 1 H), 7.10-7.20 (m, 3 H), 6.50 (s, 1 H), 4.77-4.84 (m, 1 H), 4.40-4.45 (m, 1 H), 4.34-4.39 (m, 1 H), 3.10 (s, 3 H), 2.40 (s, 3 H), 2.34 (s, 3 H), 1.39 (d, J=6.6 Hz, 3 H); LCMS Method A (ESI, positive ion spectrum): (M+H)/z=554, $t_R$=2.16 min.

Example 27

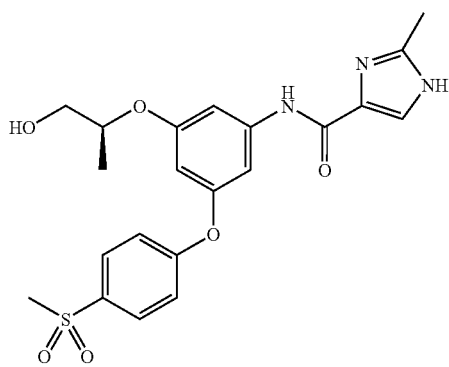

The title compound (7.1 mg, 44% yield, white solid) was prepared from Example 26 (20 mg; 0.036 mmol) using KOH according to the procedure described for the synthesis of Example 25. $^1$H NMR (400 MHz, CD$_3$OD) δ ppm 7.93 (d, J=8.8 Hz, 2 H), 7.63 (s, 1 H), 7.17-7.25 (m, 3 H), 7.13-7.15 (m, 1 H), 6.48 (t, J=2.2 Hz, 1 H), 4.43-4.52 (m, 1 H), 3.61-3.70 (m, 2 H), 3.11 (s, 3 H), 2.40 (s, 3 H), 1.29 (d, J=6.2 Hz, 3 H); LCMS Method A (ESI, positive ion spectrum): (M+H)/z=446, $t_R$=2.26 min.

Example 28

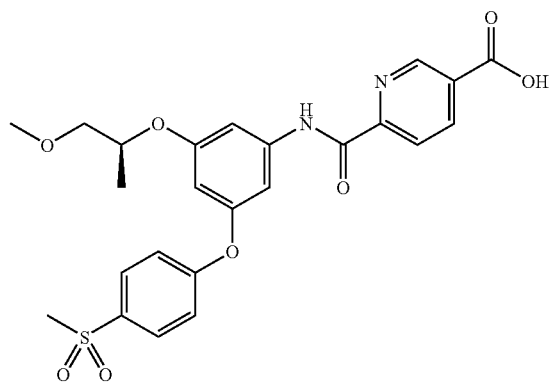

LiOH.H$_2$O (6 mg, 0.14 mmol) was added to a solution of Example 16 (24 mg, 0.047 mmol) in THF (0.4 mL) and H$_2$O (0.2 mL) at RT. The reaction was stirred at RT overnight, then was diluted with EtOAc (50 mL). The organic phase was extracted with H$_2$O (3×20 mL). The combined aqueous layers were adjusted to pH ~3 with 1N aqueous HCl and were extracted with EtOAc (3×50 mL). The combined organic extracts were washed with brine (10 mL), dried (MgSO$_4$) and concentrated in vacuo. The crude product was purified by preparative HPLC (YMC reverse phase ODS-A-5 μm 30×100 mm column; flow rate=40 mL/min, continuous gradient from 4:1 A:B to 100% B over 12 min, then held at 100% B for 3 min; where solvent A=90:10:0.1 H$_2$O:MeOH:TFA and solvent B=90:10:0.1 MeOH:H$_2$O:TFA) to afford the title compound (16.1 mg, 69% yield) as a white solid. $^1$H NMR (500 MHz, CD$_3$OD) δ ppm 9.24 (s, 1 H), 8.52-8.56 (m, 1 H), 8.28 (d, J=8.2 Hz, 1 H), 7.94 (d, J=8.8 Hz, 2 H), 7.40 (s, 1 H), 7.29 (s, 1 H), 7.21 (d, J=8.8 Hz, 2 H), 6.52 (s, 1 H), 4.57-4.66 (m, 1 H), 3.55-3.60 (m, 1 H), 3.50-3.55 (m, 1 H), 3.39 (s, 3 H), 3.11 (s, 3 H), 1.31 (d, J=6.6 Hz, 3 H); LCMS Method A (ESI, positive ion spectrum): (M+H)/z=501, $t_R$=3.29 min.

Example 29

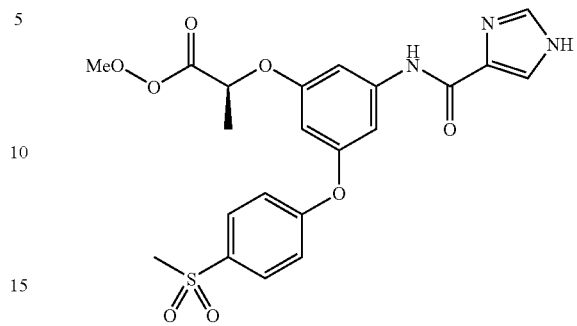

A.

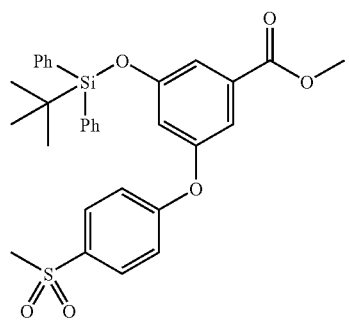

To a RT solution of methyl 3-hydroxy-5-(4-(methylsulfonyl)phenoxy)benzoate[2] (1.25 g, 3.88 mmol) in CH$_2$Cl$_2$ (20 mL) was added imidazole (581 mg, 8.54 mmol), followed by TBDPS-Cl (1.2 mL, 4.66 mmol). The reaction mixture was stirred at RT overnight, then was partitioned between EtOAc (200 mL) and H$_2$O (20 mL). The aqueous layer was extracted with EtOAc (2×20 mL). The combined organic extracts were washed with brine (10 mL), dried (MgSO$_4$), and concentrated in vacuo. The residue (a beige oil) was chromatographed (SiO$_2$; 120 g; continuous gradient from hexane to 7:3 hex:EtOAc over 40 min, held at 7:3 hex:EtOAc for 20 min) to give Part A compound (1.98 g, 91% yield) as a white solid. LCMS Method A (ESI, positive ion spectrum): (M+H)/z=561, $t_R$=4.44 min.

B.

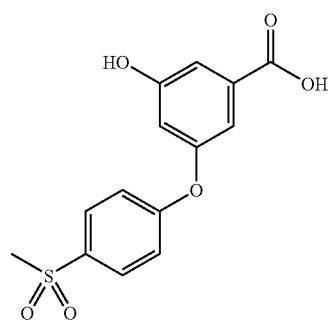

LiOH.H$_2$O (444 mg, 10.59 mmol) was added to a solution of Part A compound (1.98 g, 3.53 mmol) in THF (24 mL) and H$_2$O (12 mL) at RT. The reaction was stirred at RT overnight.

The reaction was diluted with EtOAc (50 mL). The organic layer was extracted with H₂O (3×20 mL). The combined aqueous layers were adjusted to pH ~3 with 1N aqueous HCl and extracted with EtOAc (3×100 mL). The combined organic extracts were washed with brine (10 mL), dried (MgSO₄) and concentrated in vacuo to give Part B compound (1.08 g, 99%) as a white solid. ¹H NMR (500 MHz, CD₃OD) δ ppm 7.94 (d, J=8.8 Hz, 2 H), 7.31 (s, 1 H), 7.17 (d, J=8.8 Hz, 2 H), 7.14 (s, 1 H), 6.72 (s, 1 H), 3.11 (s, 3 H); LCMS Method A (ESI, positive ion spectrum): (M+H)/z=309, $t_R$=2.25 min.

C.

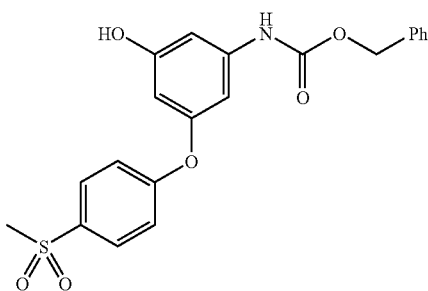

To a RT solution of Part B compound (1.0 g, 3.24 mmol) in 1,4-dioxane (16 mL) were added benzyl alcohol (0.40 mL, 3.89 mmol), Et₃N (0.63 mL, 4.54 mmol) and (PhO)₂PON₃ (0.84 mL, 3.89 mmol) with stirring. The reaction mixture was stirred at 120° C. overnight, then cooled to RT. Volatiles were removed in vacuo and the residue was chromatographed (SiO₂; 120 g; continuous gradient from hexane to 1:1 hex:EtOAc over 40 min, then held at 1:1 hex:EtOAc for 20 min) to give Part C compound (0.65 g, 49% yield) as a white solid. ¹H NMR (500 MHz, CDCl₃/CD₃OD) δ ppm 7.83 (d, J=8.8 Hz, 2 H), 7.28-7.38 (m, 5 H), 7.07 (d; J=8.8 Hz, 2 H), 6.82 (s, 1 H), 6.54-6.59 (m, 1 H), 6.23 (s, 1 H), 5.14 (s, 2 H), 3.02 (s, 3 H); LCMS Method A (ESI, positive ion spectrum): (M+H)/z=414, $t_R$=3.10 min.

D.

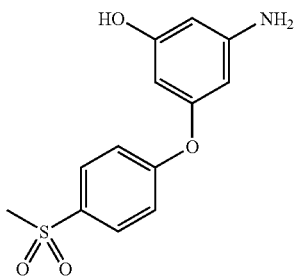

To a solution of Part C compound (150 mg, 0.36 mmol) in MeOH (10 mL) was added 10% Pd/C (15 mg) under Ar at RT with vigorous stirring. The reaction was stirred under 1 atm of H₂ for 3 h, then was filtered through Celite®. Volatiles were removed in vacuo to give Part D Compound (95.9 mg, 95% yield) as a beige solid. LCMS Method. A (ESI, positive ion spectrum): (M+H)/z=280, $t_R$=1.57 min.

E.

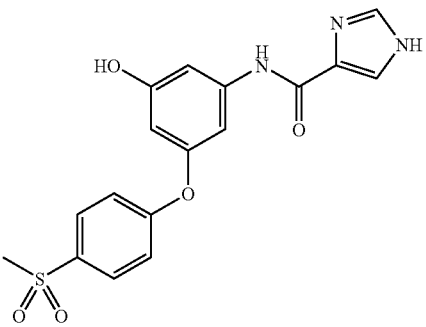

BOP (301 mg, 0.68 mmol) was added to a solution of 4-imidazolecarboxylic acid monohydrate (76 mg, 0.68 mmol) in pyridine (3 mL) at RT, followed by Et₃N (0.19 mL; 1.36 mmol). After stirring at RT for 10 min, Part D compound (95 mg, 0.34 mmol) was added. The reaction was heated at 80° C. overnight; LC-MS showed that the starting material had disappeared. The reaction mixture was diluted with MeOH (2 mL), THF (2 mL) and. H₂O (1 mL). KOH (~15 mg) was added to the reaction, which was stirred at RT for 1 h. Volatiles were removed in vacuo and the residue was partitioned between EtOAc (100 mL) and H₂O (10 mL). The pH of the aqueous layer was adjusted to ~8 with 1N aqueous HCl. The aqueous layer was extracted with EtOAc (2×10 mL). The combined organic extracts were washed with brine (5 mL), dried (MgSO₄) and concentrated in vacuo. The crude product was purified by preparative HPLC (YMC reverse phase ODS-A-5 μm 30×100 mm column; flow rate=40 mL/min, continuous gradient from 4:1 A:B to 100% B over 10 min, held at 100% B for 2 min, where solvent A=90:10 H₂O:MeOH and solvent B=90:10 MeOH:H₂O) to give Part E compound (34.2 mg, 27%) as a white solid ¹H NMR (500 MHz, CD₃OD/CDCl₃) δ ppm 7.86 (d, J=8.8 Hz, 2 H), 7.71 (s, 1 H), 7.66 (s, 1 H), 7.59 (s, 1 H), 7.15 (d, J=8.8 Hz, 2 H), 7.03-7.06 (m, 2 H), 6.30 (t, J=2.2 Hz, 1 H), 3.07 (s, 3 H); LCMS Method A (ESI, positive ion spectrum): (M+H)/z=374, $t_R$=2.20 min.

F.

Trityl chloride (29.1 mg, 0.104 mmol) was added to a solution of Part E Compound (30 mg, 0.080 mmol) in pyridine (0.2 mL) and DMF (0.4 mL) at RT. The reaction was stirred at RT overnight. Volatiles were removed in vacuo. The crude product was chromatographed (SiO₂; 4 g; continuous gradient from hexane to 1:4 hexane:EtOAc over 20 min, then held at 1:4 hexane:EtOAc for 15 min) to give Part F Compound (39 mg, 79% yield) as a white solid. ¹H NMR (500 MHz, CD₃OD) δ ppm 7.91 (d, J=8.8 Hz, 2H), 7.62 (s, 1 H), 7.57 (s, 1 H), 7.38-7.42 (m, 9 H), 7.14-7.19 (m, 8 H), 7.10

(s, 1 H), 6.98 (s, 1 H), 6.27-6.29 (m, 1 H), 3.09 (s, 3 H); LCMS Method B (ESI, pos./neg. ion spectrum): (M−H)/z =614, $t_R$=3.83 min.

G.

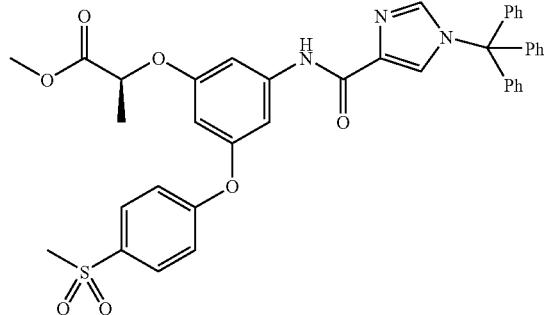

To a solution of Part F compound (32 mg, 0.052 mmol) in dry THF (0.5 mL) was added polymer-bound Ph₃P (45 mg, 0.135 mmol, 3 mmol/g) and (R)-methyl 2-hydroxy-propanoate (7.45 µL, 0.078 mmol) under Ar at RT. DIAD (0.018 mL, 0.094 mmol) was then added dropwise at 0° C. The reaction was allowed to warm to RT and stirred for 2 h. The resin was filtered off and washed with 10 mL of THF. The combined filtrates were concentrated in vacuo. The crude product was chromatographed (SiO₂; 4 g; continuous gradient from hexane to 3:7 hex:EtOAc over 20 min, then held at 3:7 hex:EtOAc for 15 min) to give Part G compound (28.8 mg, 79% yield) as a white solid. ¹H NMR (500 MHz, CDCl₃) δ ppm 8.95 (s, 1 H), 7.87 (d, J=8.8 Hz, 2 H), 7.59 (s, 1 H), 7.40 (s, 1 H), 7.32-7.37 (m, J=4.9 Hz, 9 H), 7.07-7.15 (m, 10 H), 6.36 (s, 1 H), 4.71-4.82 (m, 1 H), 3.76 (s, 3 H), 3.04 (s, 3 H), 1.60 (d, J=6.6 Hz, 3 H); LCMS Method A (ESI, positive ion spectrum): (M+H)/z=702, $t_R$=3.96 min.

H.

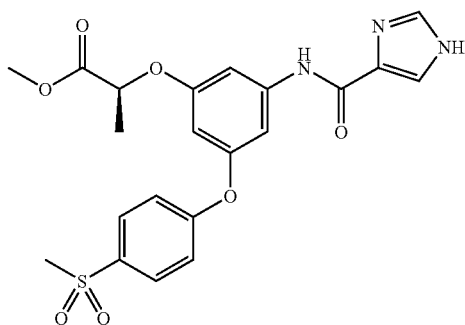

A solution of Part G Compound (26 mg, 0.037 mmol) and TFA (0.3 mL) in CH₂Cl₂ (0.6 mL) was stirred at RT for 10 min. Volatiles were evaporated in vacuo and the residue was chromatographed (SiO₂; 4 g; continuous gradient from hexane to 95:5 hex:EtOAc over 15 min, then held at 95:5 hex: EtOAc for 15 min) to give the title compound (9.5 mg, 56% yield) as a white solid. ¹H NMR (500 MHz, CDCl₃) δ ppm 8.59 (s, 1 H), 8.19 (s, 1 H), 7.81 (d, J=8.8 Hz, 2 H), 7.10 (s, 1 H), 7.04 (d, J=8.2 Hz, 2 H), 6.92 (s, 1 H), 6.33 (s, 1 H), 4.78 (q, J=6.6 Hz, 1 H), 3.78 (s, 3 H), 3.03 (s, 3 H), 1.60 (d, J=6.6 Hz, 3 H); LCMS Method. A (ESI, positive ion spectrum): (M+H)/z=460, $t_R$=2.44 min.

Example 30

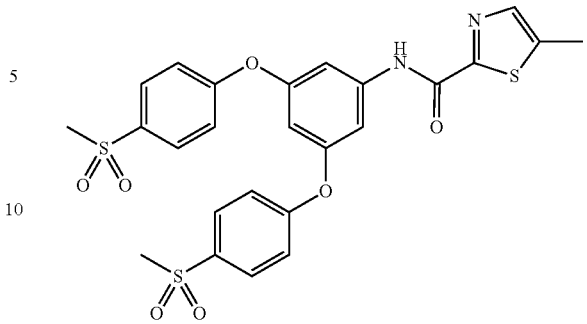

A.

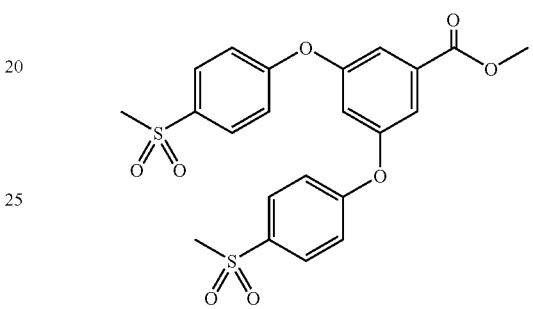

A solution of methyl 3,5-dihydroxybenzoate (2.5 g, 14.9 mmol), 1-fluoro-4-(methylsulfonyl)benzene (5.18 g, 29.8 mmol) and anhydrous K₂CO₃ (8.23 g, 59.6 mmol) in dry DMF (100 ml) was heated at 120° C. for 10 h, then was cooled to RT and filtered. The solid was washed with CH₂Cl₂ (100 mL) and the combined filtrate was concentrated in vacuo. The residue was chromatographed (SiO₂; 80 g; continuous gradient from 100% hexane to 100% EtOAc over 40 min) to provide Part A compound (6.1 g) as a white solid. LCMS Method A (ESI, positive ion spectrum): (M+H)/z=477, $t_R$=2.99 min.

B.

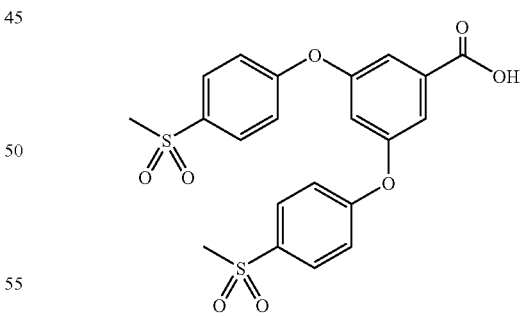

A RT solution of Part A Compound (2.3 g, 4.83 mmol), and LiOH.H₂O (4.1 g, 97.5 mmol) in THF (10 mL)/H₂O (5 mL) was stirred for 2 h. The reaction was acidified to pH ~1 with 1N aqueous HCl, extracted with EtOAc (3×15 mL). The combined organic extracts were washed with brine (30 mL), dried (MgSO₄) and concentrated in vacuo to give Part B Compound (2.2 g) as a white solid. LCMS Method B (ESI, positive and negative ion spectra): (M−H)/z=461, $t_R$=1.43 min.

C.

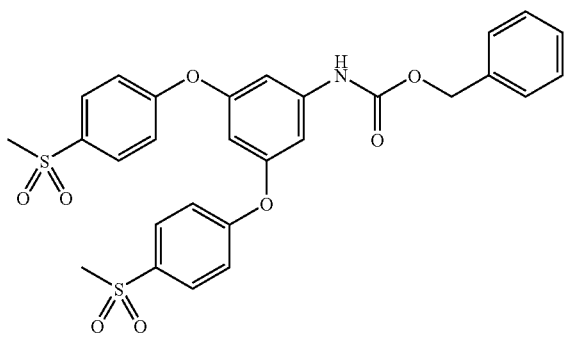

To a RT solution of Part B Compound (1 g, 2.16 mmol) in 1,4-dioxane (10 mL) was added benzyl alcohol (0.27 mL, 2.59 mmol), Et$_3$N (0.422 mL, 3.03 mmol) and (PhO)$_2$PON$_3$ (0.562 mL, 2.59 mmol). The reaction mixture was stirred at 120° C. overnight, then was cooled to RT and concentrated in vacuo. The residue was chromatographed (SiO$_2$; 120 g; continuous gradient from 100% hexane to 40:60 hex:EtOAc over 35 min, then held at 40:60 hex:EtOAc for 25 min) to give Part C Compound (782 mg, 64% yield) as a white solid. $^1$H NMR (400 MHz, DMF-d7) δ ppm 10.13 (s, 1 H), 7.95-8.08 (m, 5 H), 7.26-7.47 (m, 10 H), 6.69 (d, J=2.2 Hz, 1 H), 3.50 (d, J=2.2 Hz, 2 H), 3.26 (d, J=2.2 Hz, 6 H); LCMS Method A (ESI, positive ion spectrum): (M+H)/z=568 t$_R$=3.42 min.

D.

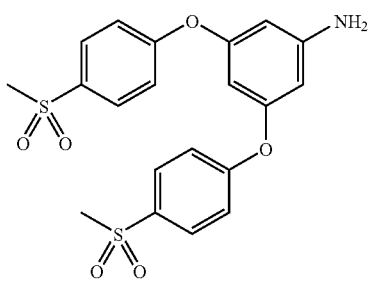

To a RT solution of Part C Compound (780 mg, 1.374 mmol) in THF (10 mL) and MeOH (30 mL) was added 10% Pd/C (78 mg) under Ar. The reaction was stirred under 1 atm of H$_2$ for 1 h, then was filtered through Celite®. The filtrate was concentrated in vacuo to give Part D Compound (597 mg, 100% yield) as a beige solid. LCMS Method A (ESI, positive ion spectrum): (M+H)/z=434, t$_R$=2.54 min.

E.

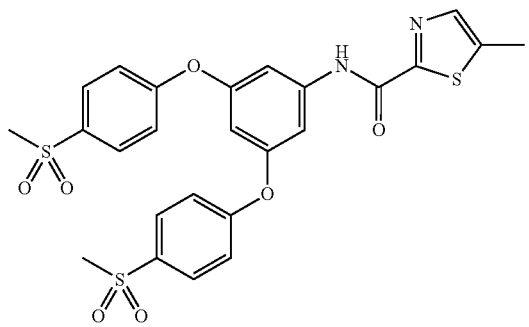

EDAC (19.90 mg, 0.104 mmol) was added to a solution of sodium 5-methylthiazole-2-carboxylate (17.1 mg, 0.104 mmol) in CH$_2$Cl$_2$ (1.0 mL) and Et$_3$N (0.014 mL, 0.104 mmol), followed by HOBT (14 mg, 0.104 mmol) and DMAP (0.85 mg, 6.92 μmol) at RT. After stirring at RT for 10 min, Part D Compound (30 mg, 0.069 mmol) was added. The reaction mixture was stirred at RT overnight; LC-MS showed that most of the starting material had been converted to the desired product. The reaction was partitioned between EtOAc (100 mL) and H$_2$O (10 mL). The aqueous layer was extracted with EtOAc (2×10 mL). The combined organic extracts were washed with brine (10 mL), dried (MgSO$_4$) and concentrated in vacuo. The crude product was chromatographed (SiO$_2$; 4 g; continuous gradient from 100% hexane to 100% EtOAc over 40 min, then held at 100% EtOAc for 10 min) to give the title compound (3.6 mg, 7% yield) as a white solid. $^1$H NMR (400 MHz, DMSO-d6) δ ppm 11.02 (s, 1 H), 7.91-7.96 (m, 4 H), 7.79 (s, 1 H), 7.60 (d, J=2.2 Hz, 2 H), 7.27-7.32 (m, 4 H), 6.74 (t, J=2.2 Hz, 1 H), 3.21 (s, 6 H), 2.53 (s, 3 H); LCMS Method A (ESI, positive ion spectrum): (M+H)/z=559, t$_R$=3.30 min.

Example 31

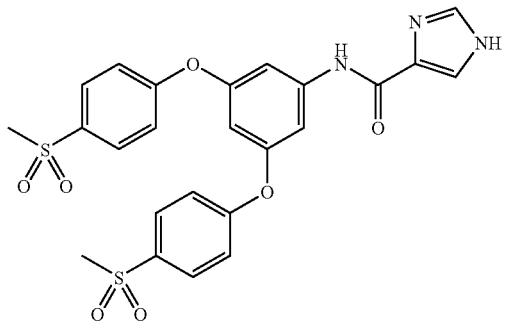

Compound 31 (21.6 mg; 44% yield; white solid) was prepared from Example 30 Part D Compound (40 mg; 0.092 mmol) using the same procedure as described for the synthesis of Example 29E. $^1$H NMR (500 MHz, DMSO-d6) δ ppm 10.22 (s, 1 H), 7.93 (d, J=8.8 Hz, 4 H), 7.80 (s, 1 H), 7.78 (s, 1 H), 7.63 (d, J=2.2 Hz, 2 H), 7.28 (d, J=8.8 Hz, 4 H), 6.64 (t, J=2.2 Hz, 1 H), 3.20 (s, 6 H); LCMS Method A (ESI, positive ion spectrum): (M+H)/z=528, t$_R$=2.52 min.

Example 32

A.

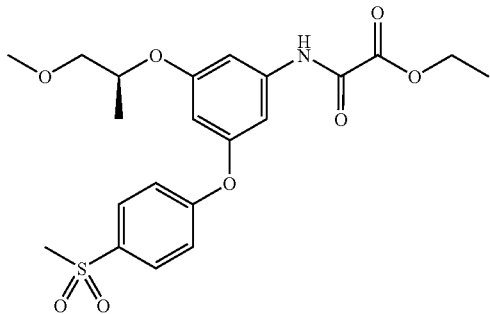

A solution of ethyl chlorooxoacetate (16 μL; 0.148 mmol), Example 1 Part B Compound (40 mg, 0.114 mmol) and Et₃N (48 μL; 0.34 mmol) in CH₂Cl₂ (1.2 mL) was stirred at RT for 2 h. The reaction mixture was chromatographed (SiO₂; 12 g; continuous gradient from 100% hex to 3:7 hex:EtOAc over 25 min, then held at 3:7 hex:EtOAc for 10 min) to give Part A Compound (40.2 mg, 78% yield) as a light yellow oil. $^1$H NMR (500 MHz, CDCl₃) δ ppm 8.83 (s, 1 H), 7.89 (d, J=8.8 Hz, 2 H), 7.10-7.14 (m, 3 H), 6.99 (s, 1 H), 6.48 (s, 1 H), 4.49-4.56 (m, 1 H), 4.38-4.43 (m, 2 H), 3.54-3.58 (m, 1 H), 3.46-3.50 (m, 1 H), 3.39 (s, 3 H), 3.05 (s, 3 H), 1.41 (t, J=7.1 Hz, 3 H), 1.30 (d, J=6.6 Hz, 3 H); LCMS Method A (ESI, positive ion spectrum): (M+H)/z=452, $t_R$=3.04 min.

B.

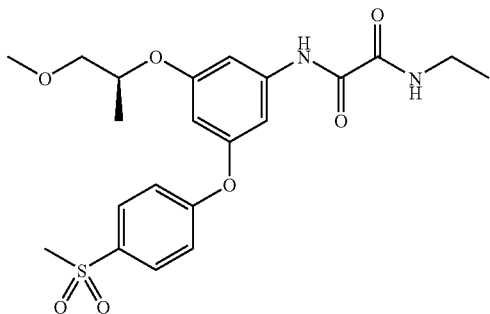

Ethylamine (1.0 mL, 2.0 M in CH₃OH) was added to Example 32 Part A Compound (21.8 mg, 0.048 mmol). The reaction mixture was stirred at RT overnight. Volatiles were removed in vacuo and the residue was chromatographed (SiO₂; 4 g; continuous gradient from 100% hex to 1:4 hex:EtOAc over 20 min, then held at 1:4 hex:EtOAc for 10 min) to give the title compound (24.6 mg, 100%) as a light yellow oil. $^1$H NMR (500 MHz, CDCl₃) δ ppm 9.23 (s, 1 H), 7.89 (d, J=8.8 Hz, 2 H), 7.46 (s, 1 H), 7.08-7.13 (m, 3 H), 7.01 (s, 1 H), 6.45-6.47 (m, 1 H), 4.47-4.55 (m, 1 H), 3.53-3.58 (m, 1 H), 3.46-3.50 (m, 1 H), 3.37-3.44 (m, 5 H), 3.05 (s, 3 H), 1.30 (d, J=6.0 Hz, 3 H), 1.23 (t, J=7.1 Hz, 3 H); LCMS Method A (ESI, positive ion spectrum): (M+H)/z=451, $t_R$=3.00 min.

Example 33

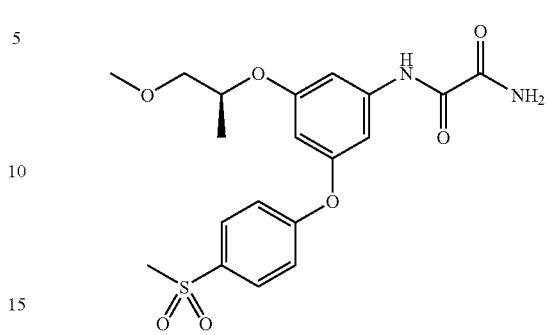

The title compound (15 mg; 95% yield; tan solid) was prepared from Example 32 Part A Compound and NH₃ in MeOH (1 mL of a 1.0 M solution) using the same procedure as that described for the synthesis of Example 32. $^1$H NMR (CDCl₃, 500 MHz) δ 9.18 (s, 1H), 7.89 (d, 2H, J=8.8 Hz), 7.36 (s, 1H), 7.11 (d, 2H, J=8.8 Hz), 7.09 (br. s, 1H), 7.02 (br. s, 1H), 6.47 (s, 1H), 5.79 (s, 1H), 4.56-4.48 (m, 1H), 3.56 (dd, 1H, J=10.5, 6.1 Hz), 3.49 (dd, 1H, J=10.5, 4.4 Hz), 3.39 (s, 3H), 3.05 (s, 3H), 1.31 (d, 3H, J=6.1 Hz) ppm; LCMS Method A (ESI, positive ion spectrum): (M+H)/z=423, $t_R$=2.70 min.

Example 34

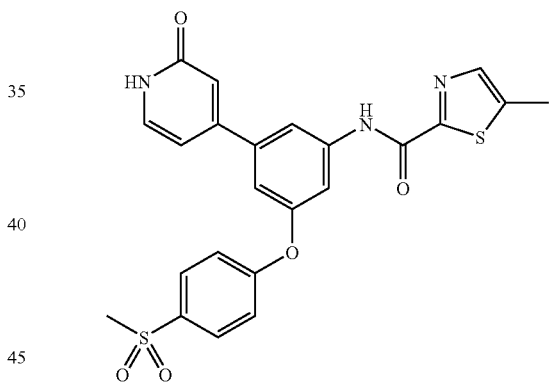

A.

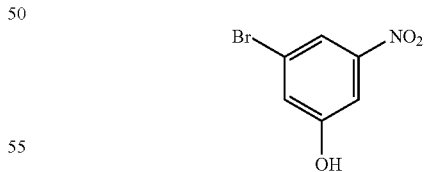

BBr₃ (8.62 mL of a 1.0 M solution in CH₂Cl₂; 8.62 mmol) was added to a solution of 1-bromo-3-methoxy-5-nitrobenzene (500 mg, 2.16 mmol) in CH₂Cl₂ (5 mL) at −20° C. The reaction was allowed to warm to RT and stirred at RT overnight, then was cautiously quenched with MeOH (30 mL) and stirred for 1 h at RT. Volatiles were removed in vacuo to give crude Part A Compound as a brown solid. $^1$H NMR (500 MHz, CDCl₃) δ ppm 7.94 (s, 1 H), 7.62-7.64 (m, 1 H), 7.33 (s, 1 H), 5.84 (s, 1 H); LCMS Method A (ESI, positive ion spectrum): (M+H)/z=220, $t_R$=3.14 min.

B.

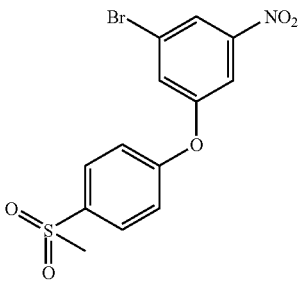

To a solution of Part A Compound (469 mg, 2.15 mmol) in DMF (4 mL) was added 1-fluoro-4-(methylsulfonyl)benzene (562 mg, 3.23 mmol) at RT, followed by $K_2CO_3$ (891 mg, 6.45 mmol). The mixture was heated at 120° C. for 48 h, then was cooled to RT. The mixture was diluted with EtOAc (50 mL), washed with $H_2O$ (20 mL) and brine (2×10 mL), dried ($MgSO_4$) and concentrated in vacuo. The residual red oil was chromatographed ($SiO_2$; 40 g; continuous gradient from 100% hex to 2:3 hex:EtOAc over 40 min, then held at 2:3 hex:EtOAc for 10 min) to give Part B Compound (474 mg, 59% yield) as a beige solid. LCMS Method A (ESI, positive ion spectrum): (M+H)/z=374, $t_R$=3.23 min.

C.

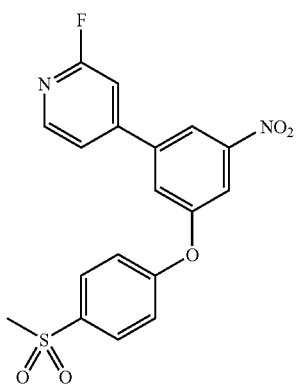

To a degassed solution of Part B Compound (120 mg, 0.322 mmol) in DME (1.6 mL)/$H_2O$ (0.4 mL) were successively added 2-fluoropyridin-4-ylboronic acid (91 mg, 0.645 mmol), $K_2CO_3$ (89 mg, 0.645 mmol) and $(Ph_3P)_4Pd(0)$ (18.6 mg, 0.016 mmol). The reaction was heated at 150° C. in an Emrys Optimizer® (microwave) for 15 min, then was cooled to RT. The reaction mixture was partitioned between EtOAc (100 mL) and $H_2O$ (10 mL). The organic phase was washed with brine (10 mL), dried ($MgSO_4$) and concentrated in vacuo. The crude product was chromatographed ($SiO_2$; 12 g; continuous gradient from 100% hex to 1:1 hex:EtOAc over 25 min, then held at 1:1 hex:EtOAc for 15 min) to give Part C Compound (100 mg, 80% yield) as a white solid. LCMS Method A (ESI, positive ion spectrum): (M+H)/z=389, $t_R$=2.99 min.

D.

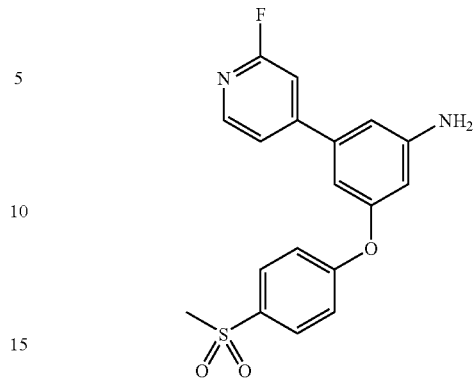

Iron dust (71.9 mg, 1.29 mmol) was added to a suspension of Part C Compound (100 mg, 0.257 mmol) in AcOH (2.5 mL). The reaction mixture was stirred at RT overnight, then was partitioned between EtOAc (100 mL) and $H_2O$ (10 mL). The aqueous layer was extracted with EtOAc (2×10 mL). The combined organic extracts were washed with saturated aqueous $NaHCO_3$ (10 mL) and brine (10 mL), dried ($MgSO_4$) and concentrated in vacuo to afford Part D Compound (96.8 mg, 100%) as a beige solid. LCMS Method A (ESI, positive ion spectrum): (M+H)/z=359, $t_R$=2.52 min.

E.

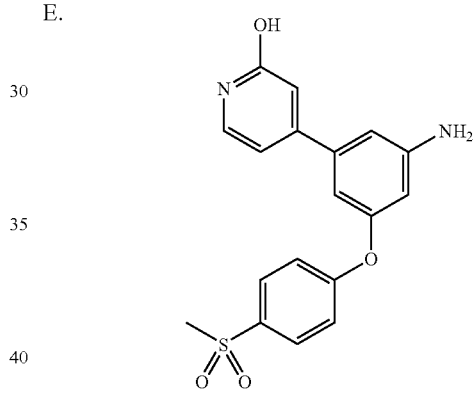

A mixture of Part D Compound (60 mg, 0.167 mmol) and 1N aqueous NaOH (1.5 mL) was heated at 160° C. in an Emrys Optimizer® (microwave) for 15 min, then was cooled to RT and partitioned between EtOAc (50 mL) and $H_2O$ (5 mL). The aqueous layer was extracted with EtOAc (2×20 mL). The combined organic extracts were washed with brine (10 mL), dried ($MgSO_4$) and concentrated in vacuo to afford Part E Compound (53.2 mg, 89% yield) as a white solid. LCMS Method A (ESI, positive ion spectrum): (M+H)/z 357, $t_R$=1.85 min.

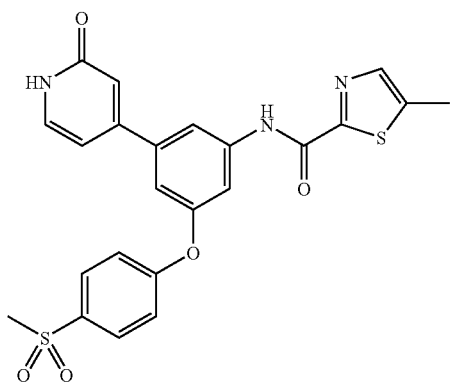

BOP (49.6 mg, 0.112 mmol) was added to a solution of sodium 5-methylthiazole-2-carboxylate (18.5 mg, 0.112 mmol) in pyridine (0.5 mL) at RT, followed by Et₃N (31 µL; 0.224 mmol). After stirring at RT for 10 min, Part E Compound (20 mg, 0.056 mmol) was added and the reaction was heated at 80° C. overnight, then was cooled to RT. Volatiles were removed in vacuo and the residue was partitioned between EtOAc (50 mL) and H₂O (5 mL). The aqueous layer was extracted with EtOAc (2×10 mL). The combined organic extracts were washed with sat. aq. NaHCO₃ (10 mL) and brine (10 mL), dried (MgSO₄) and concentrated in vacuo. The crude product was chromatographed (SiO₂; 4 g; continuous gradient from 100% CH₂Cl₂ to 9:1 CH₂Cl₂:MeOH over 20 min, then held at 9:1 CH₂Cl₂:MeOH for 15 min) to give the title compound (1.2 mg, 5% yield) as a white solid. ¹H NMR (400 MHz, CDCl₃/CD₃OD) δ ppm 7.85 (d, J=8.8 Hz, 2 H), 7.63-7.70 (m, 2 H), 7.53 (s, 1 H), 7.23-7.33 (m, 2 H), 7.10 (d, J=8.8 Hz, 2 H), 7.01 (s, 1 H), 6.68 (s, 1 H), 6.46-6.52 (m, 1 H), 3.02 (s, 3 H), 2.51 (s, 3 H); LCMS Method A (ESI, positive ion spectrum): (M+H)/z=482, t_R=3.01 min.

Example 35

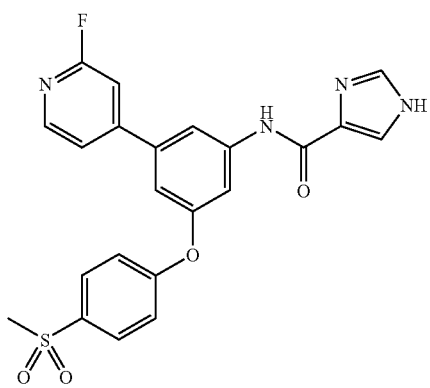

BOP (148 mg, 0.335 mmol) was added to a solution of 1H-imidazole-4-carboxylic acid (37.5 mg, 0.335 mmol) in pyridine (1.5 mL) at RT, followed by Et₃N (93 µL; 0.67 mmol). After stirring at RT for 10 min, Example 34 Part D compound (60 mg, 0.167 mmol) was added. The reaction was heated at 80° C. for 4 h, then was cooled to RT. Volatiles were removed in vacuo and the residue was partitioned between EtOAc (50 mL) and H₂O (5 mL). The aqueous layer was extracted with EtOAc (2×10 mL). The combined organic extracts were washed with sat. aq. NaHCO₃ (10 mL) and brine (10 mL), dried (MgSO₄) and concentrated in vacuo. The crude product was chromatographed (SiO₂; 12 g; continuous gradient from 100% CH₂Cl₂ to 95:5 CH₂Cl₂:MeOH over 30 min, then held at 95:5 of CH₂Cl₂:MeOH for 15 min) to give the title compound (72.7 mg, 96% yield) as a white solid. ¹H NMR (500 MHz, CD₃OD/CDCl₃) δ ppm 8.23 (d, J=5.5 Hz, 1 H), 7.89-7.94 (m, 3 H), 7.75 (s, 1 H), 7.70 (s, 1 H), 7.68 (s, 1 H), 7.55 (s, 1 H), 7.50 (d, J=5.5 Hz, 1 H), 7.20 (d, Hz, 2 H), 7.15 (s, 1 H), 3.09 (s, 3 H); LCMS Method A (ESI, positive ion spectrum): (M+H)/z=453, t_R=2.65 min.

Example 36

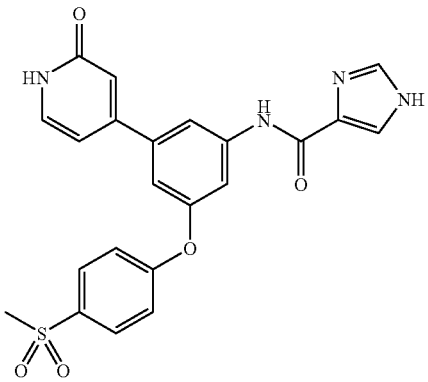

Example 35 Compound (25 mg, 0.055 mmol) was dissolved in 1N aqueous NaOH (0.3 mL) and the reaction was heated at 140° C. in an Emrys Optimizer® (microwave) for 6 min, then was cooled to RT and diluted with EtOAc (50 mL). The aqueous layer was extracted with EtOAc (2×10 mL). The combined organic extracts were washed with brine (10 mL), dried (MgSO₄) and concentrated in vacuo. The crude product was purified by preparative HPLC (YMC reverse phase ODS-A-5 µm 30×100 mm column; flow rate=40 mL/min, continuous gradient from 4:1 A:B to 100% B over 12 min, then held at 100% B for 3 min, where solvent A=90:10:0.1 H₂O:MeOH:TFA and solvent B=90:10:0.1 MeOH:H₂O:TFA) to give the title compound (6.4 mg, 26% yield) as a white solid. ¹H NMR (500 MHz, CD₃OD) δ ppm 8.77 (s, 1 H), 8.15 (s, 1 H), 7.97 (d, J=8.8 Hz, 2 H), 7.88 (s, 1 H), 7.71 (s, 1 H), 7.53 (d, J=7.1 Hz, 1 H), 7.22-7.28 (m, 3 H), 6.77 (s, 1 H), 6.71 (d, J=7.1 Hz, 1 H), 3.12 (s, 3 H); LCMS Method A (ESI, positive ion spectrum): (M+H)/z=451, t_R=2.14 min.

Example 37

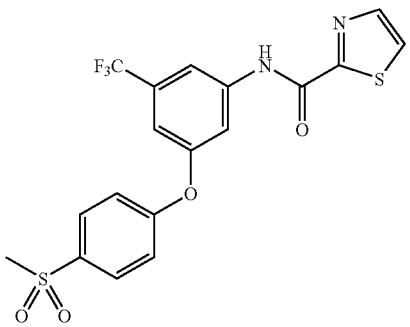

A.

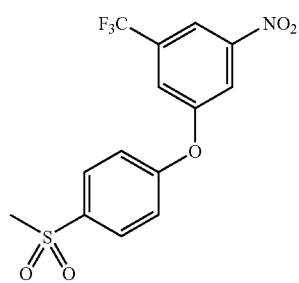

A solution of 3-nitro-5-(trifluoromethyl)phenol (207 mg, 1.0 mmol), 1-fluoro-4-(methylsulfonyl)benzene (523 mg, 3.0 mmol) and anhydrous K$_2$CO$_3$ (414 mg, 3.0 mmol) in dry DMF (100 ml) was heated at 120° C. for 3 h. The reaction was cooled to RT, filtered and washed with CH$_2$Cl$_2$ (100 mL). The filtrate was concentrated in vacuo. The crude material was chromatographed (SiO$_2$; 40 g; EtOAc/hexane) to provide Part A Compound (361 mg, 100% yield) as a white solid. $^1$H NMR (CDCl$_3$, 500 MHz) δ 8.06-7.96 (m, 2 H), 7.28-7.22 (m, 5 H), 3.06 (s, 3 H) ppm; LCMS Method A (ESI, positive ion spectrum): (M+H)/z=362, t$_R$=3.24 min.

B.

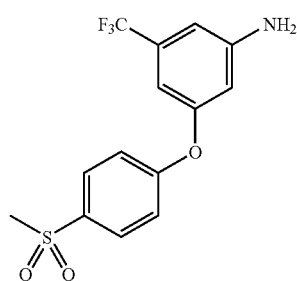

A solution of Part A Compound (361 mg, 1.0 mmol) and Pd/C (10%, 50 mg) in MeOH (3 mL) was stirred under an atmosphere of H$_2$ for 1 h. The reaction was diluted with CH$_2$Cl$_2$ (10 mL) and filtered, through Celite®. The filtrate was concentrated to afford crude Part B Compound as a tan solid (331 mg, 100% yield). This material was used in the next step without further purification. LCMS Method A (ESI, positive ion spectrum): (M+H)/z=332, t$_R$=2.99 min.

C.

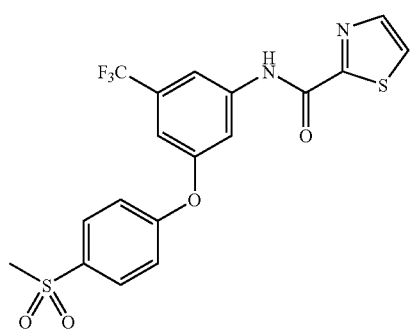

Part C compound (41 mg, 95% yield, white solid) was prepared by the reaction of Part B compound (33.1 mg; 0.1 mmol) and thiazole-2-carbonyl chloride (19 mg, 0.13 mmol) according to the procedure described for the synthesis of Example 1. $^1$H NMR (CDCl$_3$, 500 MHz) δ 9.29 (s, 1H), 8.00-7.91 (m, 3H), 7.82 (s, 1H), 7.73 (s, 1H), 7.69 (d, 1H, J=2.8 Hz), 7.16 (d, 2H, J=8.2 Hz), 7.12 (s, 1H), 3.08 (s, 3H); HPLC Method B; t$_R$=6.83 min; LCMS Method A (ESI, positive ion spectrum): (M+H)/z=433, t$_R$=3.47 min.

References

1. The required (S)-3-(1-methoxypropan-2-yloxy)-5-(4-(methylsulfonyl)phenoxy)benzoic acid was prepared according to known procedures in WO 2005/121110 and WO 2005/080359.

2. The required methyl 3-hydroxy-5-(4-(methylsulfonyl) phenoxy)benzoate was prepared according to known procedures in WO 2005/121110.

Assays and Biological Data

Compounds of formula I of the invention, including compounds described in the Examples hereof, have been tested in the following assay and have shown to be activators of glucokinase. In general, compounds of the present invention, such as particular compounds disclosed in the following examples, have been identified to enhance the activity of glucokinase at concentrations equivalent to, or more potently than, 100 μM, preferably 10 μM, more preferably 1 μM, thereby demonstrating compounds of the present invention as especially effective enhancers of activity of glucokinase. Potencies can be calculated and expressed as either EC$_{50}$ (concentration to achieve 50% of full activation) and/or the maximum percentage activation above background, and refer to activity measured employing the assay system described below.

Compounds of formula I of the invention, including compounds described in the Examples hereof, have been tested in the following assay and have shown to be activators of glucokinase.

Glucokinase Tandem Enzymatic Assay

Enzymatic activity of human glucokinase (GK) was measured by incubating GK, ATP, and glucose for discrete time periods followed by quenching with EDTA (ethylenediamine tetra-acetic acid). Relative amounts of product glucose-6-phosphate (G6P) were measured by then running a detection assay using G6P dehydrogenase and measuring the conversion of ThioNAD (thio-nicotinamide adenine dinucleotide) to ThioNADH (thio-dihydronicotinamide adenine dinucleotide) at a wavelength of 405 nm. This 'uncoupled' enzymatic reaction is denoted as the GK 'tandem' assay. Activation of GK by compounds can be assessed using this assay. The GK tandem assay protocol described below was followed using a range of activator compound concentrations from 0 to 100 μM at 5 and 12 mM of glucose. Human full-length glucokinase (GK, 15 nM) was incubated with 5 or 12 mM glucose in a 384 well black microtiter plate with a clear bottom. To initiate the GK reaction, magnesium-ATP (3 mM final concentration) was added to GK in buffer (final buffer conditions of 25 mM HEPES buffer, pH 7.1, containing 1 mM dithiothreitol and 5% DMSO). The total reaction volume was 20 μL. The reaction was allowed to proceed for ten minutes and was then quenched with 5 μL EDTA; 45 mM final). The components of the detection reaction, ThioNAD and G6PDH (glucose-6-phosphate dehydrogenase) (final concentrations of 650 μM and 3.33 Units, respectively), were then added together in a volume of 25 μL (to give a total volume of 50 μL). Absorbance measurements were made at 405 nm on a Spectramax Plus 384 absorbance plate reader (Molecular Devices). Absorbance was read, background glucose-6-phosphate levels were subtracted, after which activation was calculated as a percentage of control activity. Control activity was determined using GK in the presence of vehicle (DMSO), with background glucose-6-phosphate subtracted. Background glucose-6-phosphate was determined by pre-quenching GK with EDTA prior to reaction initiation with ATP.

Expression and Purification of Human GK

Full-length human hepatic GK (untagged) was expressed in BL21 STAR (DE3)pLysS cells (Invitrogen) at 25° C. as described by Mookhtiar et al. (1). The protein was purified essentially as described by Lange (2) with a slight modification. Briefly, cell pellets were lysed via three rounds of freezing and thawing, centrifuged at 15000 g for clarification, and precipitated with 40-65% $(NH_4)_2SO_4$. The resulting pellet was resuspended in buffer, dialyzed, and applied directly to a Q-Sepharose (Sigma) column followed by elution with a linear 100-600 mM KCl gradient. GK containing fractions were pooled, dialyzed overnight vs. 25 mM Hepes pH 7.2/1 mM $MgCl_2$/1 mM EDTA/0.1 M KCl/1 mM DTT, then dialyzed again with same buffer with 10% glycerol added.

References

1. Mookhtiar, K. A. et al., "Heterologous expression and characterization of rat liver glucokinase regulatory protein", *Diabetes*, 45:1670-1677 (1996).

2. Lange, A. J. et al., "Expression and site-directed mutagenesis of hepatic glucokinase", *Biochem. J.*, 277:159-163 (1991).

Biological data for select Examples are shown in the table below.

| Example No. | $EC_{50}$ (nM) with Human Glucokinase @ 12 mM Glucose |
|---|---|
| 18 | 67 |
| 22 | 77 |
| 5 | 165 |
| 6 | 191 |
| 8 | 513 |
| 31 | 575 |

For other Examples, the $EC_{50}$ values could not be calculated from the activation curves, so the maximal activation data (expressed as a % of basal activation) for some select Examples are shown in the table below.

| Example No. | Maximal activation (%) Human Glucokinase @ 12 mM Glucose |
|---|---|
| 7 | 131% |
| 37 | 163% |

In Vivo Studies: Oral Glucose Tolerance Test (OGTT)

Oral glucose tolerance tests were carried out on male DIO (diet-induced obese) C57BL/6J mice fed a high fat diet (60% kcal from fat) for 26 weeks prior to experimentation. Mice were fasted overnight before use for experiments. A test compound or vehicle (10% dimethyl acetamide +10% ethanol +10% Cremophore +70% water) was given orally 60 min before oral administration of a glucose solution at a dose of 2 g/kg body weight (oral glucose tolerance test; OGTT). Blood glucose levels were measured from tail-bled samples taken at different time points before and after administration of glucose (time course of 2 hours). A time curve of the blood glucose was generated and the change from baseline area-under the curve (ΔAUC) from 0-120 min was calculated (the time glucose administration being time zero). Example 6 reduced glucose AUC levels in an OGTT test in DIO mice as described above by 66% at a 30 mg/kg dose.

What is claimed is:

1. A compound of the structure

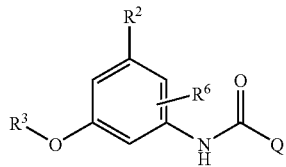

where Q is

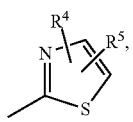

or a pharmaceutically acceptable salt thereof, and all stereoisomers thereof, including enantiomers and diastereomers thereof;

wherein $R^4$ and $R^5$ are the same or different and are independently selected from the group consisting of H, alkyl, halogen, CN, —C(O)$NR^7R^8$, —$CO_2R^9$, and -L-M-$Q_a$;

L is independently selected from O, S, $SO_2$, or is absent;

M is independently selected from $C_{1-4}$ alkyl optionally substituted with OH or $C_{2-5}$ alkylene, or M is absent;

$Q_a$ is independently selected from the group consisting of halogen, —$OR^{9b}$, —$CO_2H$, —$CO_2R^{9c}$, —C(O)$NR^7R^8$, CN, N-linked amide (—$NR^7C(O)R^8$), N-linked sulfonamide (—$NR^9SO_2R^{10}$), N-linked carbamate (—$NR^8CO_2R^{10}$), O-linked carbamate (—OCO$NR^7R^8$), and N-linked urea (—$NR^9C(O)NR^7R^8$);

$R^6$ is H, OH, $C_{1-6}$ alkyl, halogen, CN, —C(O)$NH_2$ or carboxyl, or $R^6$ is absent;

$R^7$ and $R^8$ (regardless of which group each is a part of) are the same or different and are independently selected from the group consisting of H, alkyl, cycloalkyl, aryl, arylalkyl, heteroaryl, and heteroarylalkyl, or $R^7$ and $R^8$ are cyclized together to form a 3- to 7-membered heterocycle;

$R^9$ and $R^{9c}$ (regardless of which group each is a part of) are independently selected from the group consisting of H, alkyl, aryl, and arylalkyl;

$R^{10}$ (regardless of which group it is a part of) is independently selected from the group consisting of alkyl, aryl, heteroaryl, aralkyl, and heteroarylalkyl;

$R^2$ and $R^3$ are the same or different, and are independently selected from Y—Z—;

each —Z— is independently selected from a direct bond, or a linker atom selected from the group consisting of —O—, —N($R^9$)—, —S—, —S(O)—, —S(O)$_2$—, —C(O)—, and a group of the formula —($CH_2$)$_p$—C($R^{11}$)$_2$—($CH_2$)$_q$—;

each Y is independently selected from the group consisting of aryl-$Z^1$—, heteroaryl-$Z^1$—, and heterocyclyl-$Z^1$—, where the aryl, heteroaryl or heterocyclyl is connected to $Z^1$ through a ring nitrogen or carbon;

or Y is independently selected from the group consisting of $C_{3-7}$cycloalkyl-$Z^1$—, $C_{1-6}$alkyl-$Z^1$—, $C_{2-6}$-alkenyl-$Z^1$—, $C_{2-6}$-alkynyl-$Z^1$—, —$Z^1$—CH($CH_{3-a}F_a$)$_2$, and —$Z^1$—($CH_2$)$_{0-4}$$CH_{3-a}F_a$;

wherein each Y is independently optionally substituted by up to 3 $R^{12}$ groups;

each $R^{12}$ is independently selected from the group consisting of halogen, —$CH_{3-a}F_a$, CN, $NO_2$, $NH_2$, $C_{1-6}$alkyl, $OC_{1-6}$alkyl, —COOH, OH, aryloxy, heteroaryloxy, heterocyclyloxy, —$S-R^{10}$, —$S(O)-R^{10}$, —$SO_2R^9$, —$SO_2NR^7R^8$, —$NR^7R^8-CO_2R^9$, —$C(O)N^7R^8$, N-linked amide (—$NR^7C(O)R^8$), N-linked sulfonamide)(—$NR^9SO_2R^{10}$, N-linked carbamate)(—$NR^8CO_2R^{10}$, O-linked carbamate (—$OCONR^7R^8$), N-linked urea (—$NR^9C(O)NR^7R^8$), —$(CH_2)_p$—PO$(OR^7)(OR^8)$, —$(CH_2)_p$—PO$(OR^7)R^8$, —$(CH_2)_p$—O—PO$(OR^7)R^8$, —$(CH_2)_pO$—PO—$(R^7)R^8$, —$(CH_2)_p$—P$(O)R^7R^8$, aryl, heteroaryl, and heterocyclyl;

wherein each phenyl, naphthyl, heteroaryl, or heterocyclyl ring in Y or $R^{12}$ is optionally substituted by a member selected from the group consisting of halogen, =O, =S, $C_{1-6}$alkyl, —$CH_{3-a}F_a$, CN, $NO_2$, $NH_2$, —COOH, OH, $C_{1-6}$alkyl, —$OC_{1-6}$alkyl, —$C(O)OC_{1-6}$alkyl, —$NR^{7a}R^{8a}$, —$C(O)NR^{7a}R^{8a}$, N-linked amide (—$NR^{7a}COR^{8a}$), N-linked sulfonamide (—$NR^{9a}SO_2R^{10a}$), N-linked carbamate (—$NR^{8a}COOR^{10a}$), N-linked urea (—$NR^{9a}CONR^{7a}R^{8a}$), sulfonamide (—$SO_2NR^{7a}R^{8a}$), —$(CH_2)_p$—PO$(OR^{7a})(OR^{8a})$, —$(CH_2)_p$—PO$(OR^{7a})R^{8a}$, —$(CH_2)_p$—O—PO$(OR^{7a})R^{8a}$, —$(CH_2)_pO$—PO—$(R^{7a})R^{8a}$, or —$(CH_2)_p$—P$(O)R^{7a}R^{8a}$;

each —$Z^1$— is independently selected from a direct bond, or a linker atom selected from —O—, —N($R^9$)—, —S—, —S(O)—, —$S(O)_2$—, —C(O)— or a group of the formula —$(CH_2)_p$—$C(R^{11})_2$—$(CH_2)_q$—;

$R^{11}$ is independently selected from the group consisting of hydrogen, $C_{1-6}$alkyl, halo$C_{1-6}$alkyl, and $C_{2-4}$alkyl-O—$C_{1-4}$alkyl;

each a is an integer independently selected from 1, 2, 3;

p is an integer independently selected from 0, 1 or 2;

q is an integer independently selected from 0, 1 or 2;

and p+q ≤4;

$R^{7a}$ and $R^{8a}$ are the same or different and are independently selected from the group consisting of H, alkyl, cycloalkyl, aryl, arylalkyl, heteroaryl and heteroarylalkyl or $R^{7a}$ and $R^{8a}$ cyclized together to form a 3- to 7-membered heterocyclo;

$R^{9a}$ and $R^{9b}$ are independently selected from the group consisting of H, alkyl, aryl, heterocyclyl, aralkyl, and heteroarylalkyl; and $R^{10a}$ is independently selected from the group consisting of alkyl, aryl, heteroaryl, aralkyl and heteroarylalkyl.

2. The compound as defined in claim 1 wherein $R^4$ and $R^5$ are the same or different and are independently selected from the group consisting of H, alkyl, arylalkyl, alkoxycarbonyl and carboxyl, or a pharmaceutically acceptable salt thereof, and all stereoisomers thereof, including enantiomers and diastereomers thereof.

3. The compound as defined in claim 2 wherein Q is

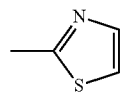

or

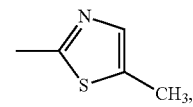

or a pharmaceutically acceptable salt thereof, and all stereoisomers thereof, including enantiomers and diastereomers thereof.

4. The compound as defined in claim 1 wherein the $R^2$ is Y—Z—, where Z is O or a bond; and Y is $C_{1-6}$alkyl-$Z^1$—where $Z^1$ is a bond, aryl-$Z^1$—where $Z^1$ is a bond, heterocyclyl-$Z^1$—where $Z^1$ is a bond, or heteroaryl-$Z^1$—where $Z^1$ is a bond, and $R^6$ is hydrogen, or a pharmaceutically acceptable salt thereof, and all stereoisomers thereof, including enantiomers and diastereomers thereof.

5. The compound as defined in claim 4 wherein the $R^2$ group is selected from the group consisting of

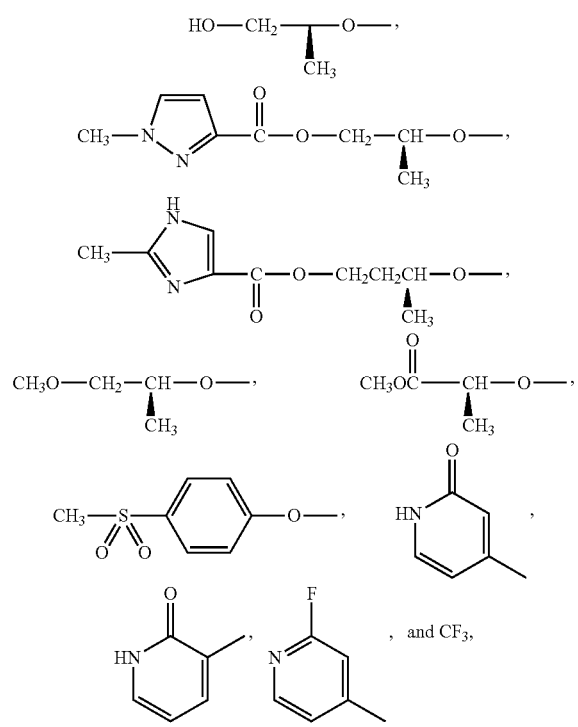

or a pharmaceutically acceptable salt thereof, and all stereoisomers thereof, including enantiomers and diastereomers thereof.

6. The compound as defined in claim 1 wherein $R^3$ is Y—Z—where Z is a bond, and Y is aryl $Z^1$ where $Z^1$ is a bond, or a pharmaceutically acceptable salt thereof, and all stereoisomers thereof, including enantiomers and diastereomers thereof.

7. The compound as defined in claim 6 wherein R³ is

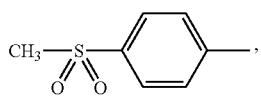

or a pharmaceutically acceptable salt thereof, and all stereoisomers thereof, including enantiomers and diastereomers thereof.

8. The compound as defined in claim 1 wherein

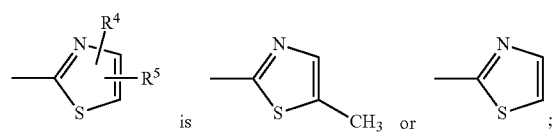 is

R² is

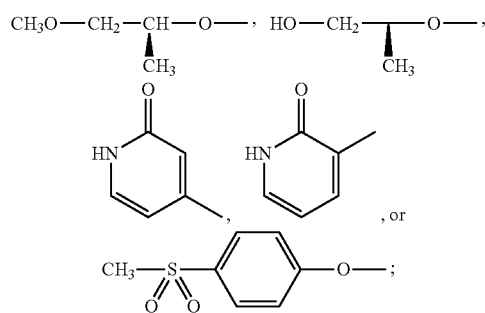

R³ is

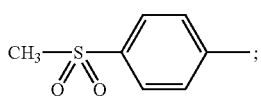

and
R⁶ is H, or a pharmaceutically acceptable salt thereof, and all stereoisomers thereof, including enantiomers and diastereomers thereof.

9. A compound of the structure

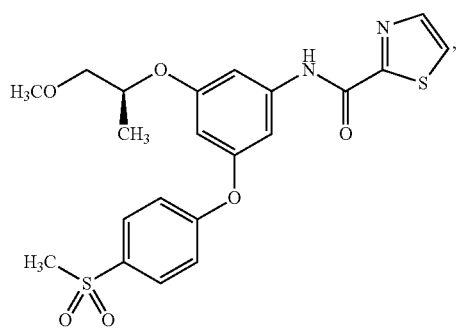

-continued

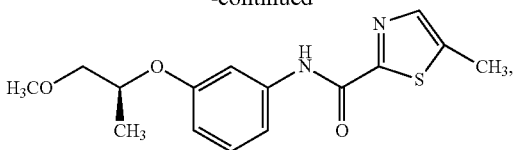

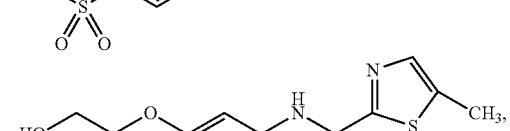

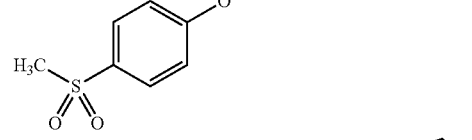

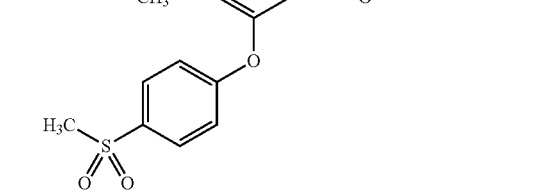

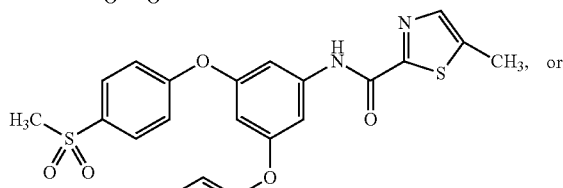

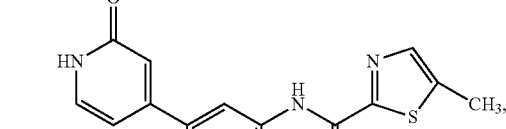

or a pharmaceutically acceptable salt thereof, and all stereoisomers thereof, including enantiomers and diastereomers thereof.

10. A pharmaceutical composition comprising a compound as defined in claim 1, or a pharmaceutically acceptable salt thereof, and all stereoisomers thereof, including enantiomers and diastereomers thereof, and a pharmaceutically acceptable carrier thereof.

11. A pharmaceutical composition comprising a compound as defined in claim 1, or a pharmaceutically acceptable salt thereof, and all stereoisomers thereof, including enantiomers and diastereomers thereof, and another therapeutic agent which is an anti-diabetic agent, anti-hyperglycemic agent, anti-hyperinsulinemic agent, anti-retinopathic agent, anti-neuropathic agent, anti-nephropathic agent, anti-atherosclerotic agent, anti-infective agent, anti-ischemic agent, anti-hypertensive agent, anti-obesity agent, anti-dyslipidemic agent, anti-hyperlipidemic agent, anti-hypertriglyceridemic agent, anti-hypercholesterolemic agent, anti-ischemic agent, anti-cancer agent, anti-cytotoxic agent, anti-restenotic agent, anti-pancreatic agent, lipid lowering agent, appetite suppressant, memory enhancing agent, or cognitive agent.

\* \* \* \* \*

UNITED STATES PATENT AND TRADEMARK OFFICE
CERTIFICATE OF CORRECTION

PATENT NO. : 8,273,777 B2  Page 1 of 1
APPLICATION NO. : 12/871226
DATED : September 25, 2012
INVENTOR(S) : Yan Shi et al.

It is certified that error appears in the above-identified patent and that said Letters Patent is hereby corrected as shown below:

On the Title Page:

Item (73), Assignee:
    Change "Bristol-Meyer Squibb Company" to -- Bristol-Myers Squibb Company --.

In the Claims:

Claim 1:
    Column 72, lines 33 and 34, change "sulfonamide)" to -- sulfonamide --.

Column 73, line 5, change "—$NR^7R^8$—$CO_2R^9$," to -- —$NR^7R^8$, —$CO_2R^9$, --.

Column 73, lines 6 and 7, change "sulfonamide)(—$NR^9SO_2R^{10}$," to -- sulfonamide (—$NR^9SO_2R^{10}$), --.

Column 73, lines 7 and 8, change "carbamate)(—$NR^8CO_2R^{10}$," to -- carbamate (—$NR^8CO_2R^{10}$), --.

Column 73, line 30, change "—C(O)—or" to -- —C(O)—, or --.

Signed and Sealed this
Fourteenth Day of May, 2013

Teresa Stanek Rea
*Acting Director of the United States Patent and Trademark Office*